(12) United States Patent
Blommel et al.

(10) Patent No.: US 9,873,836 B2
(45) Date of Patent: *Jan. 23, 2018

(54) PROCESS FOR CONVERTING BIOMASS TO AROMATIC HYDROCARBONS

(71) Applicant: Virent, Inc., Madison, WI (US)

(72) Inventors: Paul Blommel, Oregon, WI (US); Andrew Held, Madison, WI (US); Ralph Goodwin, Madison, WI (US); Randy Cortright, Madison, WI (US)

(73) Assignee: Virent, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/285,158

(22) Filed: May 22, 2014

(65) Prior Publication Data

US 2014/0349361 A1 Nov. 27, 2014

Related U.S. Application Data

(60) Provisional application No. 61/826,358, filed on May 22, 2013.

(51) Int. Cl.
| | | |
|---|---|---|
| C07C 1/20 | (2006.01) | |
| C10G 3/00 | (2006.01) | |
| C10G 1/00 | (2006.01) | |
| C12P 5/00 | (2006.01) | |
| C12F 3/02 | (2006.01) | |
| C12P 7/02 | (2006.01) | |

(Continued)

(52) U.S. Cl.
CPC .............. *C10G 1/002* (2013.01); *C10G 1/00* (2013.01); *C10G 3/42* (2013.01); *C10G 3/49* (2013.01); *C12F 3/02* (2013.01); *C12P 5/005* (2013.01); *C12P 7/02* (2013.01); *C12P 7/10* (2013.01); *C12P 7/40* (2013.01); *C10G 2300/1011* (2013.01); *C10G 2300/1025* (2013.01); *C10G 2400/30* (2013.01); *Y02E 50/16* (2013.01); *Y02P 30/20* (2015.11)

(58) Field of Classification Search
None
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |

(Continued)

FOREIGN PATENT DOCUMENTS

| | | |
|---|---|---|
| GB | 1446522 | 8/1976 |
| GB | 1526461 | 9/1978 |

(Continued)

OTHER PUBLICATIONS

International Search Report and Written Opinion for PCT/US2014/039154 dated Aug. 27, 2014.

(Continued)

*Primary Examiner* — Philip Louie
(74) *Attorney, Agent, or Firm* — Quarles & Brady LLP

(57) ABSTRACT

The present invention provides methods, reactor systems, and catalysts for increasing the yield of aromatic hydrocarbons produced while converting biomass to hydrocarbons. The invention includes methods of using catalysts to increase the yield of benzene, toluene, and mixed xylenes in the hydrocarbon product.

20 Claims, 11 Drawing Sheets

100 Raw feedstock processing
102 Conversion
104 Conditioning
106 Condensation

(51) Int. Cl.
*C12P 7/10* (2006.01)
*C12P 7/40* (2006.01)

(56) References Cited

U.S. PATENT DOCUMENTS

| | | | |
|---|---|---|---|
| 3,832,449 | A | 8/1974 | Rosinski et al. |
| 3,894,103 | A | 7/1975 | Chang |
| 3,894,104 | A | 7/1975 | Chang |
| 3,894,105 | A | 7/1975 | Chang |
| 3,894,106 | A | 7/1975 | Chang |
| 3,907,915 | A | 9/1975 | Chang |
| 3,998,898 | A | 12/1976 | Chang |
| 4,016,245 | A | 4/1977 | Plank et al. |
| 4,039,600 | A | 8/1977 | Chang |
| 4,076,761 | A | 2/1978 | Chang |
| 4,076,842 | A | 2/1978 | Plank et al. |
| 4,107,195 | A | 8/1978 | Rollmann |
| 4,139,600 | A | 2/1979 | Rollmann et al. |
| 4,359,587 | A | 11/1982 | Abdurakhmanov |
| 4,375,573 | A | 3/1983 | Young |
| 5,019,663 | A | 5/1991 | Chou et al. |
| 7,022,888 | B2 | 4/2006 | Choudhary et al. |
| 7,767,867 | B2 | 8/2010 | Cortright |
| 7,898,664 | B2 | 3/2011 | Cortright |
| 7,977,517 | B2 | 7/2011 | Cortright et al. |
| 8,053,615 | B2 | 11/2011 | Cortright et al. |
| 8,153,850 | B2 | 4/2012 | Hall et al. |
| 2007/0244208 | A1* | 10/2007 | Shulenberger ............ C01B 3/34 518/726 |
| 2009/0287019 | A1* | 11/2009 | Hazin .................... B01J 23/002 562/598 |
| 2010/0077655 | A1* | 4/2010 | Bauldreay ................. C10L 1/04 44/437 |
| 2010/0197959 | A1* | 8/2010 | Johnston ................. C07C 67/00 560/265 |
| 2011/0294163 | A1* | 12/2011 | Li ............................. C12P 7/10 435/72 |
| 2012/0035390 | A1* | 2/2012 | Gadewar ................. B01D 3/001 560/239 |

FOREIGN PATENT DOCUMENTS

| | | |
|---|---|---|
| JP | 50-076027 | 6/1975 |
| JP | 52-008005 | 1/1977 |
| JP | 57-102835 | 6/1982 |
| WO | 2010065643 A2 | 6/2010 |
| WO | 2012162403 A1 | 11/2012 |

OTHER PUBLICATIONS

Chen, N. Y. et al. "Liquid fuel from carbohydrates." Chemtech 16.8 (1986): 506-511.

Zhang, Huiyan, et al. "Catalytic conversion of biomass-derived feedstocks into olefins and aromatics with ZSM-5: the hydrogen to carbon effective ratio." Energy & Environmental Science 4.6 (2011): 2297-2307.

Fuhse, Jürgen et al. "Conversion of organic oxygen compounds and their mixtures on H-ZSM-5." Chemical engineering & technology 10.1 (1987): 323-329.

Chen, N. Y., et al. "Fluidized-bed upgrading of wood pyrolysis liquids and related compounds." 1988. 277-289.

* cited by examiner

PROCESS FOR CONVERTING BIOMASS TO AROMATIC HYDROCARBONS

CROSS-REFERENCE TO RELATED APPLICATIONS

This application claims benefit of U.S. Provisional Application Ser. No. 61/826,358 filed on May 22, 2013, which is incorporated by reference herein in its entirety.

TECHNICAL FIELD

The present invention is directed to processes and systems for producing aromatic hydrocarbons at increased yields, including benzene, toluene, xylenes (dimethylbenzenes), ethylbenzene, paraxylene, metaxylene, orthoxylene and other $C_9$ aromatics.

BACKGROUND OF THE INVENTION

Aromatic hydrocarbons, notably benzene, toluene, and xylenes are important industrial commodities used to produce numerous chemicals, fibers, plastics, and polymers, including styrene, phenol, aniline, polyester, and nylon. Typically, such aromatic hydrocarbons are produced from petroleum feedstocks using well-established refining or chemical processes. More recently, there is a growing interest in providing aromatic hydrocarbons from alternative resources, such as biomass, synthesis gases and natural gas.

One type of alternative resource is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose.

The resulting composition of the biomass provides roughly 40-50% cellulose, 20-25% hemicellulose, and 25-35% lignin, by weight percent. Cellulose is typically the primary sugar source for bioconversion processes and includes high molecular weight polymers formed of tightly linked glucose monomers. Hemicellulose is generally considered a secondary sugar source and includes shorter polymers formed of various sugars. Lignin includes phenylpropanoic acid moieties polymerized in a complex three-dimensional structure and is often viewed as a waste material or byproduct useful for other processes. Collectively, the components of cellulose, hemicellulose, and lignin are often referred to as oxygenated hydrocarbons.

Heterogeneous catalysts have shown great promise for converting oxygenated hydrocarbons into fuels and chemicals. The main challenge is how to obtain high yields of select hydrocarbons while minimizing coke formation and catalyst deactivation.

Chen et al. developed the hydrogen to carbon effective ("$H:C_{eff}$") ratio as a tool to assist in determining the suitability of oxygenated hydrocarbon feedstocks for catalytic conversion to hydrocarbons using zeolite catalysts (N. Y. Chen, J. T. F. Degnan and L. R. Koeing, Chem. Tech. 1986, 16, 506). The $H:C_{eff}$ ratio is based on the amount of carbon, oxygen and hydrogen in the feed, and is calculated as follows:

$$H:C_{eff} = \frac{H - 2O}{C} \qquad \text{(equation 1)}$$

where H represents the number of hydrogen atoms, O represents the number of oxygen atoms, and C represents the number of carbon atoms. The $H:C_{eff}$ ratio applies both to individual components and to mixtures of components, but is not valid for components which contain atoms other than carbon, hydrogen, and oxygen. For mixtures, the C, H, and O are summed over all components exclusive of water and molecular hydrogen. The term "hydrogen" refers to any hydrogen atom while the term "molecular hydrogen" is limited to diatomic hydrogen, $H_2$.

Zhang et al. studied the impact of the H:Ceff ratio on the conversion of various biomass-derived oxygenated hydrocarbons to coke, olefins and aromatics using a ZSM-5 catalyst (Zhang et al., Catalytic conversion of biomass-derived feedstocks into olefins and aromatics with ZSM-5: the hydrogen to carbon effective ratio, Energy Environ. Sci., 2011, 4, 2297). Zhang reported that biomass-derived feedstocks having H:Ceff ratios of between 0 and 0.3 produced high levels of coke, making it non-economical to convert such feedstocks to aromatics and chemicals. However, by hydroprocessing the feedstock to add hydrogen, Zhang was able to produce aromatics and olefins using a ZSM-5 catalyst at yields 2 to 3 times higher than a process without hydrogenation. Specifically, Zhang reported that the aromatic and olefin yields increased from 12% to 24% and 15% to 56%, respectively, with increasing $H:C_{eff}$ ratio. The ratio of olefins to aromatics also increased with increasing $H:C_{eff}$ ratio, with the olefin yield higher than the yield of aromatics for all feedstocks. It was also reported that there is an inflection point at a H:Ceff ratio of 1.2, where the aromatic and olefin yield does not increase further, indicating that at most the yield of high value aromatic chemicals, such as benzene, toluene, and xylenes (BTX), may be limited to 24% when using zeolite catalysts according to the Zhang process.

In another study by Fuhse and Bandermann, the researchers studied the conversion of a number of different types of oxygenates over a ZSM-5 catalyst to aromatic hydrocarbons (Fuhse and Bandermann, Conversion of Organic Oxygen Compounds and their Mixtures on H-ZSM-5, Chem. Eng. Technol., 1987, 10, 323-329). The researchers reported oxygenates having H:Ceff ratios less than 1.6 cause the problem of coking, decreasing the catalyst's lifetime, but also that conversion of carboxylic acids and esters cannot be explained solely by the $H:C_{eff}$ ratio because these types of reactants undergo the side reactions of decarbonylation, decarboxylation, and ester pyrolysis. For example, the researchers reported that the reaction of acetic acid yields only acetone and CO2. Moreover, when the researchers investigated mixtures, the researchers stated that the conversion of mixtures to products depends on the individual components.

As a result, there exists a need for methods and systems to effectively and efficiently convert biomass-derived feedstocks to aromatic hydrocarbons.

SUMMARY OF THE INVENTION

The invention is generally directed to making aromatic hydrocarbons by conditioning a feedstock to provide an oxygenate mixture having a $H:C_{eff}$ ratio between 0.8 and 1.8. One aspect of the invention is a method for producing aromatic hydrocarbons, the method comprising: (a) processing a raw feedstock to form an intermediate feedstock; (b) converting the intermediate feedstock to a feedstock stream comprising an alcohol, a carboxylic acid, or combinations thereof; (c) conditioning the feedstock stream to provide an oxygenate mixture having a H:$C_{eff}$ ratio of between 0.8 and 1.8; and (d) exposing the oxygenate mixture to a condensation catalyst to produce aromatic hydrocarbons.

In certain embodiments, the intermediate feedstock comprises oxygenated hydrocarbons, alkanes, alkenes, $CO_x$ molecules, hydrogen, or combinations thereof. In certain embodiments, the converting step (b) comprises fermentation, hydrogenolysis, hydrolysis, pyrolysis, aqueous phase reforming, alcohol synthesis, Fisher-Tropsch synthesis, steam reforming, partial oxidation, hydroformylation, carbonylation, or combinations thereof. In a particular embodiment, step (b) comprises the steps of: fermenting the intermediate feedstock with one or more species of microorganism to form a fermentation broth comprising alcohols or carboxylic acids; removing the alcohols or carboxylic acids from the fermentation broth to provide the feedstock stream; and purifying the feedstock stream prior to exposing the oxygenate mixture to the conditioning catalyst.

In certain embodiments, the raw feedstock is biomass, natural gas, coal, or petroleum. In certain embodiments, the processing step (a) comprises sugar processing, biomass deconstruction, gasification, pyrolysis, combustion, liquefaction, steam reforming, cracking, partial oxidation, or combinations thereof.

In certain embodiments, the alcohol is selected from the group consisting of a primary alcohol, a secondary alcohol, a polyhydric alcohol, and combinations thereof. In particular embodiments, the alcohol may be selected from the group consisting of methanol, ethanol, n-propanol, iso-propanol, n-butanol, 2-butanol, isobutanol, n-pentanol, n-hexanol, ethylene glycol, propylene glycol, glycerol, erythritol, threitol, sugar alcohols, and combinations thereof.

In certain embodiments, the carboxylic acid is selected from the group consisting of mono-carboxylic acid, di-carboxylic acid, hydroxycarboxylic acid, and combinations thereof. In particular embodiments, the carboxylic acid is selected from the group consisting of formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, muconic acid, citric acid, and combinations thereof.

In certain embodiments, the conditioning step (c) comprises exposing the feedstock stream to a conditioning catalyst at a conditioning temperature and a conditioning pressure to produce the oxygenate mixture. In particular embodiments, the conditioning catalyst is (i) a dehydrogenation catalyst comprising a support and a metal selected from the group consisting of Cu, Ru, Ag, CuCr, CuZn, Co, alloys thereof, and combinations thereof; or (ii) a hydrogenation catalyst comprising a support and a member selected from the group consisting of Fe, Ru, Co, Pt, Pd, Ni, Re, Cu, alloys thereof, and a combination thereof. The dehydrogenation catalyst support may also comprise a material selected from the group consisting of alumina, silica, silica-alumina, titania, carbon, zirconia, zinc aluminate, and mixtures thereof. The hydrogenation catalyst support may also comprise a member selected from group consisting of a carbon, silica, alumina, zirconia, titania, vanadia, ceria, silica-aluminate, zeolite, kieselguhr, hydroxyapatite, zinc oxide, magnesium oxide, chromia, and mixtures thereof. The hydrogenation catalyst may further comprise a member selected from the group consisting of Ag, Au, Cr, Zn, Mn, Mg, Ca, Cr, Sn, Bi, Mo, W, B, P, alloys thereof, and a combination thereof. In certain embodiments, the conditioning catalyst is a dehydrogenation catalyst and (i) the conditioning temperature is between about 80° C. and 500° C.; (ii) the conditioning pressure ranges from atmospheric pressure to about 1000 psig; or both (i) and (ii). In other embodiments, the conditioning catalyst is a hydrogenation catalyst and (i) the conditioning temperature is in the range of about 80° C. to 350° C.; (ii) the conditioning pressure is in the range of about 50 psig to 5000 psig; or both (i) and (ii).

In certain embodiments, the condensation catalyst is a zeolite. In particular embodiments, the condensation catalyst is (i) a ZSM-5 catalyst; (ii) modified by a material selected from the group consisting of phosphorous, gallium, zinc, nickel, tungsten, and mixtures thereof; (iii) contained within a binder selected from the group consisting of clay, alumina, silica, silica-alumina, titania, zirconia, aluminum phosphate, and mixtures thereof; or any combination of (i), (ii), and (iii). In certain embodiments (i) the condensation temperature is between about 250° C. and 550° C.; (ii) the condensation pressure ranges from less than atmospheric pressure to about 1000 psig; or both (i) and (ii).

In certain embodiments, greater than 40%, or greater than 45%, or greater than 50%, or greater than 60%, of the carbon in the feedstock stream is contained in the aromatic hydrocarbons. In particular embodiments, the aromatic hydrocarbons are selected from the group consisting of benzene, toluene, orthoxylene, metaxylene, paraxylene, ethylbenzen, $C_9$ aromatics, and combinations thereof.

One aspect of the invention is that a portion of the feedstock stream is less than 100 years old as calculated from the carbon 14 concentration of the feedstock stream.

In certain embodiments, the oxygenate mixture comprises two or more members selected from the group consisting of an alcohol, a carboxylic acid, an ester, a ketone, and an aldehyde.

In certain embodiments, hydrogen is produced by step (a), step (b), step (c), step (d), or combinations thereof. In particular embodiments, hydrogen is produced by exposing the feedstock stream to the conditioning catalyst at the conditioning temperature and the conditioning pressure. The method may also further comprise the step of recovering the hydrogen and processing the hydrogen to provide a hydrogen stream having a hydrogen concentration of greater than 90 mol %. The method may also further comprise the step of recovering the hydrogen and processing the hydrogen to provide a hydrogen stream having a hydrogen concentration of greater than 90 mol %.

In certain embodiments, $CO_x$ molecules are produced by step (a), step (b), step (c), step (d), or combinations thereof. In particular embodiments, the fermenting of the intermediate feedstock produces $CO_2$ and the $CO_2$ is recovered to provide a $CO_2$ stream having a $CO_2$ concentration of greater than 50%. In other embodiments, a hydrogen stream is combined with $CO_x$ molecules to produce hydrocarbons, alcohols, carboxylic acids, or combinations thereof. In particular embodiments, a hydrogen stream is combined with $CO_x$ molecules to produce methane, methanol, ethanol, or combinations thereof. In other embodiments, a hydrogen stream is combined with the $CO_2$ stream produced by the fermenting of the intermediate feedstock to produce hydrocarbons, alcohols, carboxylic acids, or combinations thereof. In other embodiments, a hydrogen stream is combined with the $CO_2$ stream produced by the fermenting of the intermediate feedstock to produce methane, methanol, ethanol, or combinations thereof. In other embodiments, a hydrogen stream is combined with the $CO_x$ molecules to produce methane and wherein a portion of the conditioning heat requirement is provided by the methane-producing reaction. In other embodiments, a hydrogen stream is combined with the $CO_2$ stream produced by the fermenting of the biomass-derived feedstock to produce methane and wherein a portion of the conditioning heat requirement is provided by the methane-producing reaction.

In certain embodiments, hydrocarbons are produced by step (a), step (b), step (c), step (d), or combinations thereof. In certain embodiments, an oxygen stream is combined with the hydrocarbons to produce alcohols, carboxylic acids, or combinations thereof. In particular embodiments, an oxygen stream is combined with the hydrocarbons to produce methanol, ethanol, or combinations thereof.

In certain embodiments, a portion of the conditioning heat requirement is provided by heat generated in step (d).

Another aspect of the invention is a method for producing biomass-derived aromatic hydrocarbons, the method comprising: (a) processing biomass to form a biomass-derived feedstock; (b) converting the biomass-derived feedstock to a feedstock stream comprising an alcohol or carboxylic acid; (c) conditioning the feedstock stream to provide an oxygenate mixture having an H:Ceff ratio of between 0.8 and 1.8; and (d) exposing the oxygenate mixture to a condensation catalyst at a condensation pressure and a condensation temperature to produce aromatic hydrocarbons.

Another aspect of the invention is a method for producing biomass-derived aromatic hydrocarbons, the method comprising: (a) processing biomass to form a biomass-derived feedstock; (b) fermenting the biomass-derived feedstock with one or more species of microorganism to form a fermentation broth comprising alcohols; (c) removing the alcohols from the fermentation broth to provide a feedstock stream comprising one or more of a primary alcohol, methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols; (d) exposing the feedstock stream to a dehydrogenation catalyst at a dehydrogenation temperature and a dehydrogenation pressure to produce diatomic hydrogen and an oxygenate mixture having an $H:C_{eff}$ ratio of between 0.8 and 1.8; and (e) exposing the oxygenate mixture to a condensation catalyst at a condensation pressure ranging from less than atmospheric pressure to about 1000 psig and a condensation temperature of between about 250° C. and 550° C. to produce aromatic hydrocarbons.

Another aspect of the invention is a method for producing biomass-derived aromatic hydrocarbons, the method comprising: (a) processing biomass to form a biomass-derived feedstock; (b) fermenting the biomass-derived feedstock with one or more species of microorganism to form a fermentation broth comprising carboxylic acids; (c) removing the carboxylic acids from the fermentation broth to provide a feedstock stream comprising one or more of a mono-carboxylic acid, a di-carboxylic acid, formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, muconic acid, itaconic acid, or citric acid; (d) exposing the feedstock stream to hydrogen and a hydrogenation catalyst at a hydrogenation temperature and a hydrogenation pressure to produce an oxygenate mixture having an $H:C_{eff}$ ratio of between 0.8 and 1.8; and (e) exposing the oxygenate mixture to a condensation catalyst at a condensation pressure ranging from less than atmospheric pressure to about 1000 psig and a condensation temperature of between about 250° C. and 550° C. to produce aromatic hydrocarbons.

Another aspect of the invention is a method for producing biomass-derived aromatic hydrocarbons, the method comprising: (a) processing a first biomass to form a first biomass-derived feedstock, and fermenting the first biomass-derived feedstock with one or more species of microorganism to form a fermentation broth comprising carboxylic acids; and removing the carboxylic acids from the fermentation broth to provide a first feedstock stream comprising one or more of a mono-carboxylic acid, a di-carboxylic acid, formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, muconic acid, itaconic acid, or citric acid; (b) processing a second biomass to form a second biomass-derived feedstock, and fermenting the second biomass-derived feedstock with one or more species of microorganism to form a fermentation broth comprising alcohols; and removing the alcohols from the fermentation broth to provide a second feedstock stream comprising one or more of a primary alcohol, methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols; (c) combining a portion of the first feedstock stream with a portion of the second feedstock stream to provide an oxygenate mixture having an $H:C_{eff}$ ratio of between 0.8 and 1.8; and (d) exposing the oxygenate mixture to a condensation catalyst at a condensation pressure ranging from less than atmospheric pressure to about 1000 psig and a condensation temperature of between about 250° C. and 550° C. to produce aromatic hydrocarbons.

DETAILED DESCRIPTION OF THE INVENTION

The present invention relates to continuous processes and systems for producing aromatic hydrocarbons at high yields. The invention also includes methods and catalysts to produce aromatic hydrocarbons, including benzene, toluene, xylene (dimethylbenzene), ethyl benzene, para xylene, meta xylene, ortho xylene and other $C_9$ aromatics, at high yields. An aspect of the invention is that the aromatic hydrocarbons may be derived from a raw feedstock derived from alternative resources, such as biomass, synthesis gases and natural gas.

Figure 1:
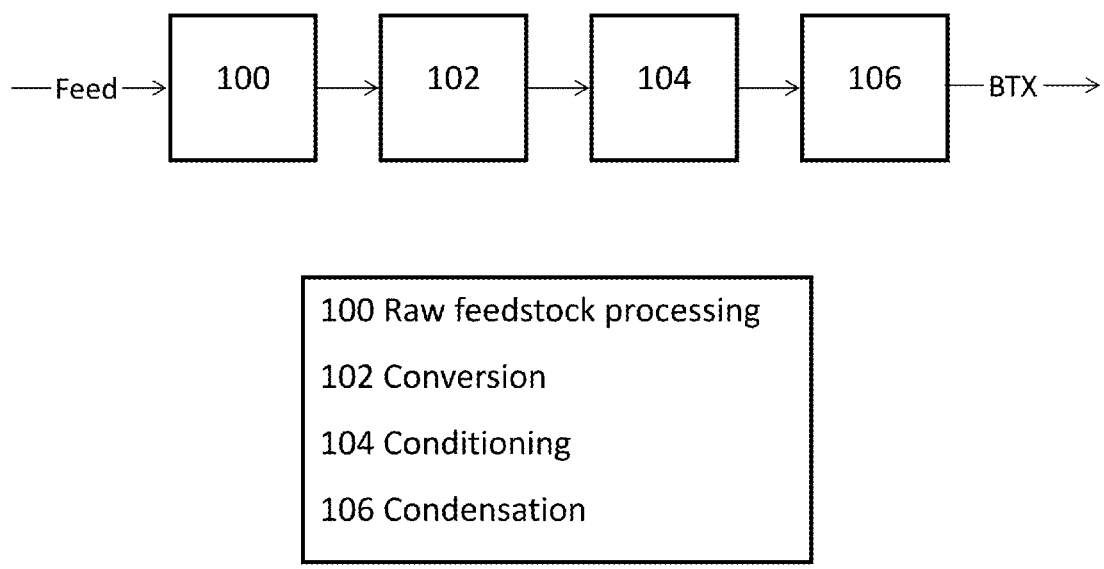
FIG. 1 is a schematic diagram of one embodiment of the present invention.
Figure 2:
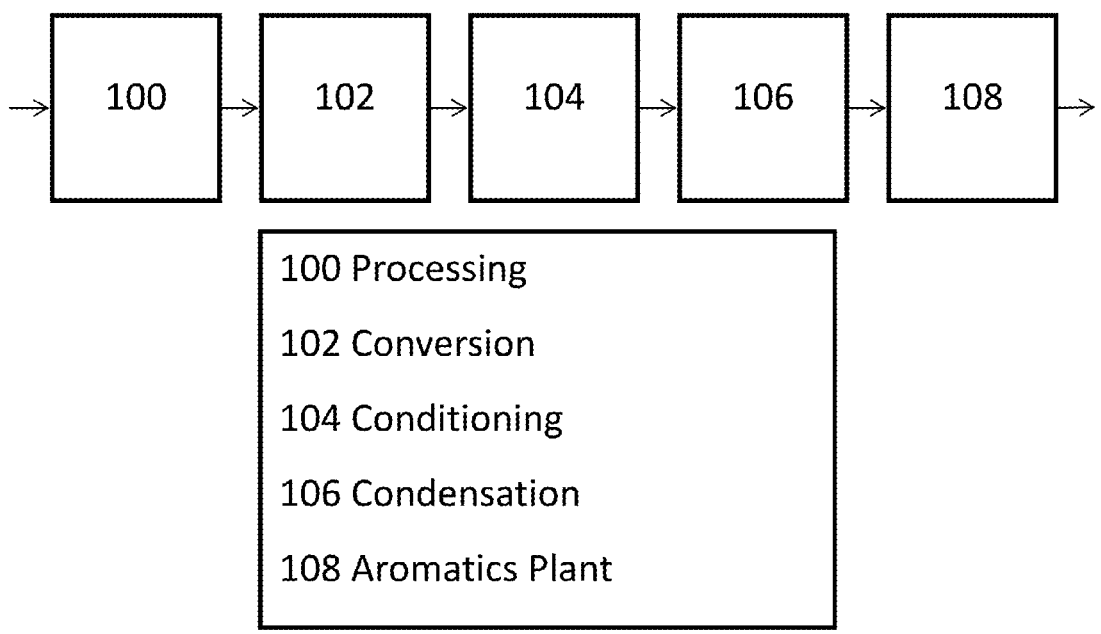
FIG. 2 is a schematic diagram of one embodiment of the present invention including an integrated aromatics complex.

As illustrated in FIG. 1, the method generally involves: (1) a raw feedstock processing step for the preparation of an intermediate feedstock; (2) a conversion step for converting the intermediate feedstock to a feedstock stream containing one or more alcohols, carboxylic acids, or combinations thereof; (3) a conditioning step for converting the feedstock stream to an oxygenate mixture having an H:$C_{eff}$ ratio of between 0.8 and 1.8; and (4) exposing the oxygenate mixture to a condensation catalyst at a condensation temperature and a condensation pressure to produce an aromatic hydrocarbons. By performing the conditioning step, aromatic hydrocarbons may be produced with yields greater than those achieved in processes converting oxygenate mixtures having an H:$C_{eff}$ ratio outside of the range of between 0.8 and 1.8. In one embodiment, the raw feedstock is biomass, and the intermediate feedstock is a biomass-derived feedstock. Alternatively, as illustrated in FIG. 2, the method may further include the processing of a stream of aromatic hydrocarbons to provide one or more product streams containing relatively pure benzene, toluene, mixed xylenes (dimethylbenzenes), ethylbenzene, paraxylene, metaxylene or orthoxylene.

As used herein, the term "oxygenates" refers to, without limitation, molecules of the general formula $C_L H_M O_N$ where L, M, and N are greater than or equal to one. In certain embodiments L is between 1 and 6, including L equal to 1, 2, 3, 4, 5, or 6; M is between 1 and 2L+2, including M equal to 1, 2, 3, 4, 5, 6, 7, 8, 9, 10, 11, 12, 13, or 14; and N is between 1 and 6, including N equal to 1, 2, 3, 4, 5, or 6. The oxygenates may also include, without limitation, alcohols, carboxylic acids, esters, aldehydes, or ketones.

As used herein, the term "alcohols" refers to, without limitation, aliphatic alcohols. In certain embodiments, the alcohols have the general formula $C_n H_{2n+2} O_1$, but may also include molecules having two or more hydroxyl moieties, such as glycols, glycerols, polyhydric alcohols, and/or sugar alcohols. A person of ordinary skill in the art will be able to determine the formula for alcohols having two or more hydroxyl moieties. Alcohols suitable for use in feedstocks in accord with the invention include $C_1$ to $C_6$ alcohols, including primary, secondary, tertiary, or polyhydric alcohols. Examples include, without limitation, one or more of methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols. If tertiary alcohols are used, they should be combined with primary or secondary alcohols.

The term "carboxylic acids" refers to, without limitation, organic acids characterized by the presence of at least one carboxyl group. The general formula of the carboxylic acid is R—COOH, where R is a functional group containing hydrogen; carbon and hydrogen; or carbon, hydrogen, and oxygen. In one embodiment, the carboxylic acid has the formula $C_n H_{2n+1} C(\!\!=\!\!O)OH$, but may also include molecules having two or more carboxyl moieties. Carboxylic acids may also include other moieties containing oxygen, such as carbonyl and/or hydroxyl moieties. A person of ordinary skill in the art will be able to determine the formula for carboxylic acids having two or more moieties containing oxygen. Carboxylic acids suitable for use as feedstocks in accord with the invention include $C_1$ to $C_6$ mono-carboxylic, di-carboxylic acids, and tri-carboxylic acids. Carboxylic acids may also include, without limitation, oxocarboxylic acids or hydroxycarboxylic acids. Examples include, without limitation, one or more of formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, itaconic acid, muconic acid, and citric acid.

The term "ester" refers to, without limitation, an organic compound with the structure RC(=O)OR', where R and R' can be a variety of hydrocarbon substituents. Esters feature a carboxyl group C(=O)O bonded to two carbon atoms. In one embodiment, the ester has a formula $C_n H_{2n+1} C(\!\!=\!\!O) OC_{n'} H_{2n'+1}$. Esters may also include other moieties containing oxygen, such as carbonyl and/or hydroxyl moieties. A person of ordinary skill in the art will be able to determine the formula for esters having two or more moieties containing oxygen. Esters suitable for use as feedstocks in accord with the invention include esters having $C_1$ to $C_6$ R and/or $C_1$ to $C_6$ R' substituents, hydroxyesters and oxoesters. Examples of esters include, without limitation, one or more of methyl formate, methyl acetate, methyl propanoate, methyl butanoate, methyl pentanoate, methyl hexanoate, ethyl formate, ethyl acetate, ethyl propanoate, ethyl butanoate, ethyl pentanoate, ethyl hexanoate, propyl formate, propyl acetate, propyl propanoate, propyl butanoate, propyl pentanoate, propyl hexanoate, butyl formate, butyl acetate, butyl propanoate, butyl butanoate, butyl pentanoate, butyl hexanoate, pentyl formate, pentyl acetate, pentyl propanoate, pentyl butanoate, pentyl pentanoate, pentyl hexanoate, hexyl formate, hexyl acetate, hexyl propanoate, hexyl butanoate, hexyl pentanoate, hexyl hexanoate, hydroxy esters thereof, and oxoesters thereof.

The term "aldehyde" refers to, without limitation, an organic compound with the structure RC(=O)H, where R can be a variety of hydrocarbon substituents. Aldehydes feature a carbonyl group (C=O) bonded to one other carbon atom and a hydrogen atom. In one embodiment, the aldehyde has a formula $C_n H_{2n+1} C(\!\!=\!\!O)H$, but may also include molecules having two or more carbonyl moieties, or other moieties containing oxygen, such a hydroxyl moiety. A person of ordinary skill in the art will be able to determine the formula for aldehydes having two or more moieties containing oxygen. Aldehydes suitable for use as feedstocks in accord with the invention include $C_1$ to $C_6$ aldehydes, dialdehydes, hydroxyaldehydes, or ketoaldehydes. Examples of ketones include, without limitation, one or more of formaldehyde, acetaldehyde, propanal, butanal, pentanal, hexanal, 1,2-ethandial, 1,3-propandial, 1,4-butandial, 1,5-pentandial, 1,6-hexandial, 2-oxopropanal, 2-oxobutanal, 3-oxopropanal, 2-oxopentanal, 3-oxopentanal, 4-oxopentanal, 2-oxohexanal, 3-oxohexanal, 4-oxohexanal, 5-oxohexanal, 2-hydroxylethanal, 2-hydroxypropanal, 3-hydroxypropanal, 2-hydroxybutanal, 3-hydroxybutanal, 4-hydroxybutanal, 2-hydroxypentanal, 3-hydroxypentanal, 4-hydroxypentanal, 5-hydroxypentanal, 2-hydroxyhexanal, 3-hydroxyhexanal, 4-hydroxyhexanal, 5-hydroxyhexanal, or 6-hydroxyhexanal.

The term "ketone" refers to, without limitation, an organic compound with the structure RC(=O)R', where R and R' can be a variety of hydrocarbon substituents. Ketones feature a carbonyl group (C=O) bonded to two other carbon atoms. In one embodiment, the ketone has a formula $C_nH_{2n+1}C(=O)C_{n'}H_{2n'+1}$, but may also include molecules having two or more carbonyl moieties or other moieties containing oxygen, such a hydroxyl moiety. A person of ordinary skill in the art will be able to determine the formula for ketones having two or more moieties containing oxygen. Ketones suitable for use as feedstocks in accord with the invention include $C_3$ to $C_6$ ketones, whether symmetric or asymmetric. Examples of ketones suitable for use in accordance with this invention include, without limitation, hydroxyketones, diketones, and one or more of acetone, butanone, pentanone, hexanone, hydroxyacetone, hydroxybutanone, hydroxypentanone, hydroxyhexanone, butandione, pentandione, hexandion, and isomers thereof.

The term "alkane" refers to, without limitation, an organic compound $C_LH_M$ where L and M are greater than or equal to one. In certain embodiments, L is between 1 and 6, including L equal to 1, 2, 3, 4, 5, or 6; and M is between 1 and 2L+2, including M equal to 1, 2, 3, 4, 5, 6, 7, 8, 9, 10, 11, 12, 13, or 14. Examples of alkanes in accord with the invention include $C_1$ to $C_6$ alkanes, whether linear or branched. Examples, include, without limitation, methane, ethane, propane, butane, 2-methylpropane, pentane, 2,2-dimethylpropane, 2-methylbutane, hexane, 2-methylpentane, 3-methylpentane, 2,2-dimethylbutane, and 2,2-methylbutane.

The term "alkene" refers to, without limitation, an organic compound $C_LH_M$ where L and M are greater than or equal to one. In certain embodiments, L is between 2 and 6, including L equal to 2, 3, 4, 5, or 6; and M is between 1 and 2L, including M equal to 1, 2, 3, 4, 5, 6, 7, 8, 9, 10, 11, 12, 13, or 14. Examples of alkanes in accord with the invention include $C_2$ to $C_6$ alkenes, whether linear or branched or whether the alkene has one or more double bonds. Examples include, without limitation, ethene, propene, 1-butene, 2-butene, 1,3-butadiene, 2-methyl-1-propene, 1-pentene, 2-pentene, 1,3-pentadiene, 1,4-pentadiene, 2-methyl-1-butene, 2-methyl-1,3-butadiene, 2-methyl-2-butene, hexenes, hexadienes, methylpentenes, methylpentadienes, and dimethylbutenes.

The term "aromatic hydrocarbons" refers to, without limitation, aromatic hydrocarbons in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl, or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aromatic hydrocarbons include, without limitation, benzene, toluene, xylenes (dimethylbenzenes), ethyl benzene, para xylene, meta xylene, ortho xylene, and $C_9$ aromatics.

Biomass Conversion

The components of the feedstock stream (e.g., alcohols, aldehydes, ketones, esters, and carboxylic acids) may originate from any source, but in one embodiment are derived from a raw feedstock of biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, pine, switch grass, alfalfa, prairie bluestream, corn, soybean, and the like. The term also refers to the primary building blocks of the above, namely, saccharides, lignin, cellulosics, hemicellulose and starches, among others.

Referring to FIGS. 1-6, the biomass is processed into a biomass-derived intermediate feedstock containing sugars and other soluble oxygenates in biomass processing step 100. For raw feedstocks (e.g., sugar cane, grain starch, sugarbeets, etc.), various sugar processing methods are well known in the art and commercially practiced at large scale. For example, in processes using sugar cane, the sugar cane is generally washed, crushed or diffused, and lime clarified to isolate and provide an aqueous biomass-derived intermediate feedstock stream rich in sucrose, fructose, and glucose. In processes using sugar beets, the sugar beets are likewise washed, sliced, extracted, and clarified to isolate and provide an aqueous biomass-derived intermediate feedstock stream in sucrose, fructose, and glucose. For processes involving cereal grains, the cereal grain is cleaned and then processed to provide wet milled starches (corn) or dry milled/ground starches (corn, wheat, barley, sorghum grain).

For a raw feedstock of lignocellulosic biomass, the biomass processing step 100 deconstructs complex biopolymers into sugars and soluble oxygenates. In one embodiment, the raw lignocellulosic feedstock (such as corn stover) undergoes deconstruction by dilute acid thermochemical pretreatment, pH adjustment by base such as ammonium hydroxide, lime, sodium hydroxide or potassium hydroxide and enzymatic hydrolysis to form soluble sugars. Optional preconversion methods include fractionation in the harvesting of the feedstock, fractionation by sieving, chemical preprocessing to leach out undesired components, fermentative preprocessing such as treatment by white rot fungi, mechanical methods such as steam explosion, torrefaction, or pelleting. Alternate means of deconstruction include thermochemical pretreatment by autohydrolysis (hot water only), alkali (for example, ammonia, sodium hydroxide, potassium hydroxide), oxidation (for example, peroxide, oxygen, air), organosolv (for example, ethanol, acetic acid, catalytically-derived solvents), and ionic liquids. The processing step 100 may also include additional processing to provide biomass that has been chopped, shredded, pressed, ground or processed to a size amenable for conversion.

Once prepared, the biomass-derived intermediate feedstock is converted in conversion step 102 to a feedstock stream containing one or more alcohols, ketones, aldehydes, esters, or carboxylic acids. The conversion may be performed using any one or more methods known in the art.

Such methods include, without limitation, fermentation, hydrogenolyis of sugars, hydrolysis of triglycerides, gasification followed by mixed alcohol synthesis reactions to produce $C_{2-10}$ alpha alcohols, pyrolysis technologies which produce alcohol or carboxylic acid streams, aqueous phase reforming or other catalytic conversion processes. In one embodiment, the components of the feedstock stream are produced using catalytic reforming technologies, such as the BioForming® technology developed by Virent, Inc. (Madison, Wis.), and described in U.S. Pat. No. 7,767,867 (Cortright), U.S. Pat. No. 7,898,664 (Cortright), U.S. Pat. No. 8,053,615 (Cortright et al.), U.S. Pat. No. 8,017,818 (Cortright et al.), and U.S. Pat. No. 7,977,517 (Cortright et al.), all of which are incorporated herein by reference. Beyond thermochemical pretreatment, alternative deconstruction methods include gasification, pyrolysis, hydrothermal liquefaction, solvolysis, and catalytic deconstruction. These methods are able to produce a mixture of water soluble oxygenates from the lignin, cellulose and hemicellulose components of biomass, and generally produce oxygenates with a lower hydrogen to carbon effective ratio.

In another embodiment, the components of the feedstock stream are produced using a fermentation process. Fermentation processes to produce alcohols, aldehydes, ketones, esters, and/or carboxylic acids from biomass are well known in the art, and generally include (1) pretreating the biomass under well-known conditions to loosen lignin and hemicellulosic material from cellulosic material, (2) breaking down the cellulosic material into fermentable saccharide material by the action of a cellulase enzyme, and (3) fermentation of the saccharide material, typically by the action of a fermenting organism, such as yeast or one of various bacterium, algae or fungi capable of producing the desired alcohols, ketones or carboxylic acids. Microorganisms known to produce such compounds from sugars include gram positive and gram negative enteric bacteria (e.g. *Bacillus* sp., *Lactobacillus* sp., *Clostridia* sp., *Escherichia* sp.), yeasts (e.g. *Saccharomyces* sp., *Pichia* sp.), fungi, and algae.

In one embodiment, the conditioning and condensation process of the present invention is integrated with a fermentation process, wherein the fermentation process produces one or more of the components of the feedstock stream used for later conditioning. The term "integrated" is intended to mean that the feedstock component is produced at a fermentation facility or within a fermentation process that is linked to a facility which performs the conditioning and condensation process described herein. To minimize production costs in some embodiments, the fermentation process is in close enough proximity to the conditioning/condensation facility, or includes appropriate conduits for transferring the feedstock stream to the facility, thereby not requiring the feedstock to be shipped. In particular embodiments, the fermentation stream produced in the fermentation facility is directly transferred to the conditioning/condensation facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermenting system to produce the feedstock components. In other embodiments, the fermentation process is part of a larger biomass conversion facility, i.e., where biomass is decomposed into fermentable saccharides, which are then processed in a fermentation zone.

In other embodiments, the components of the feedstock stream are produced from a more direct sugar source, such as a plant-based source of sugars, such as sugar cane or a grain starch (such as corn starch). Integration of the instant conditioning/condensation process with any of these large scale production methods is contemplated herein.

In some embodiments, the biomass conversion step 102 can be combined with part of the biomass treatment step 100, such as simultaneous saccharification and fermentation (SSF) in which hydrolytic enzymes are combined with the fermentation. Key benefits are fewer process steps, reduced inhibition by the fermentation intermediates (cellobiose inhibits cellulases), and better controls for contamination through the conversion of monomeric sugars as soon as produced, rather than additional steps requiring the transfer of the sugars to another processing step where contamination may occur.

The components of the feedstock stream produced by the biomass conversion step 102 may also be recovered, purified and/or concentrated prior to further processing in conditioning step 104. The nature of the recovery and purification will be depend on the specific feedstock components and the required specifications for conditioning step 104. Volatile feedstock components, such as alcohols, aldehydes and ketones (or their low-boiling azeotropes), may also be stripped from fermentation broths using heat and then recovered through the subsequent condensing of component vapors. Optionally, less volatile feedstock components, such as polyols and lower organic acids, may be recovered by using vacuum distillation, or made volatile by the addition of an entrainer. Less volatile components may also be converted into volatile derivative products using reactive separation. For example, organic acids can be reacted with alcohols to form volatile esters which can be recovered and purified by distillation.

Feedstock purification may also optionally include solid-resin-based purification systems, such as ion exchange or chromatography practiced in a fixed bed or simulated moving bed, liquid ion exchangers, chemical precipitation, electrodialysis, carbonation, chemical adsorbants such as activated carbon, hydrodemetalization, reactive extraction, liquid-liquid extraction, microfiltration, ultrafiltration, nanofiltration, and reverse osmosis.

For lignocellulosic feedstocks, the biomass treatment step 100 may also include deconstruction by gasification to produce a synthesis gas (syngas) containing mainly $H_2$ and CO, followed by fermentation of the syngas directly to produce ethanol with byproduct organic acids. The syngas may also be catalytically converted to a mixture of alcohols.

Alternative Feedstocks

Although one aspect of the present invention includes the production of aromatic hydrocarbons from biomass-derived feedstocks, other embodiments may be practiced with feedstocks derived from alternative sources, including raw feedstocks of petroleum, coal, natural gas, or any other sources. Methods for processing raw feedstocks from petroleum, coal, natural gas, or other sources include, without limitation, sugar processing, biomass deconstruction, gasification, pyrolysis, combustion, liquefaction, steam reforming, cracking, partial oxidation, or any method described herein (e.g., processing, conversion, conditioning or condensation), or combinations thereof. The raw feedstocks may be processed to produce an intermediate feedstock comprising oxygenated hydrocarbon, alkanes, alkenes, $CO_x$ molecules, hydrogen, synthesis gas (syngas), or combinations thereof. Processes for converting an intermediate feedstock to oxygenates (such as alcohols and carboxylic acids) include, without limitation, fermentation, hydrogenolysis, hydrolysis, pyrolysis, aqueous phase reforming, alcohol synthesis, Fisher-Tropsch synthesis, steam reforming, partial oxidation, hydroformylation, carbonylation, or combinations thereof.

In certain embodiments, an intermediate feedstock comprising oxygenated hydrocarbons, alkanes, alkenes, $CO_x$ molecules, hydrogen, synthesis gas (syngas), or combinations thereof, may be produced as a byproduct of any of the processes described herein, including, without limitation, the processing of the raw feedstock to produce an intermediate feedstock, converting the intermediate feedstock to an oxygenate, conditioning the oxygenate to produce the conditioned mixture, or by exposing the conditioned mixture to the condensation catalyst. The intermediate feedstock produced may be used as a reactant in any of the other methods described herein, including converting the intermediate feedstock to an oxygenate such as an alcohol or a carboxylic acid. By capturing and using byproducts of the process, the overall efficiency and/or carbon utilization may be maximized.

Feedstock Conditioning

Surprisingly, the aromatic hydrocarbon yield can be increased by conditioning the feedstock stream to provide an oxygenate mixture having an H:$C_{eff}$ ratio of between 0.8 and 1.8. In one embodiment, the oxygenate mixture has a hydrogen to carbon effective ratio of less than 1.8, 1.75, 1.7, 1.65, 1.6, 1.55, 1.5, 1.45, or 1.4. In another embodiment, the oxygenate mixture has a hydrogen to carbon effective ratio of greater than 0.8, 0.85, 0.9, 0.95, 1.0, 1.05, 1.1, 1.15, 1.2, 1.25, 1.3, 1.35, 1.4, 1.45, or 1.5. In yet another embodiment, the oxygenate mixture has a hydrogen to carbon effective ratio between 1.0 and 1.8, 1.05 and 1.75, 1.1 and 1.7, 1.15 and 1.65, or 1.2 and 1.6. Water and molecular hydrogen (diatomic hydrogen, $H_2$) are excluded from the calculation. The H:$C_{eff}$ ratio applies both to individual components and to mixtures of components, but is not valid for components which contain atoms other than carbon, hydrogen, and oxygen. For mixtures, the carbon, hydrogen, and oxygen atoms are summed over all components exclusive of water and molecular hydrogen.

Without being bound to any particular theory, the inventors believe that hydrogen atoms made available through the conversion of relatively hydrogen-rich alcohols to aromatics can be transferred to unsaturated components. If the hydrogen is transferred to an olefin, a paraffin is generated. Because olefins are precursors to aromatics, the conversion of an olefin to a paraffin reduces the available pool of material that is able to be converted to aromatics. If the hydrogen is transferred to a ketone or aldehyde, an alcohol is formed. In this manner, the carbonyl group of the ketone or aldehyde acts as a hydrogen sink, removing reactive hydrogen and preventing the conversion of olefins to paraffins, thereby reducing the amount of paraffins and increasing the overall aromatics yield.

In the case of carboxylic acid feedstocks, it is believed that hydrogen atoms, made available through the conversion of relatively hydrogen-deficient carboxylic acids to alcohols, esters, ketones and aldehydes, allows reaction pathways to be exploited across the condensation catalyst that are not feasible for an isolated carboxylic acid feedstock. These reaction pathways include reactions (such as dehydration) that can directly lead to olefin intermediates. Additional olefin intermediates may be indirectly generated through the release and transfer of hydrogen as aromatics are formed and the hydrogen released by the formation of aromatics is transferred to unsaturated oxygenates such as esters, ketones, aldehydes, and carboxylic acids.

As used herein, oxygenates capable of reacting with hydrogen in the manner described above are termed "hydrogen acceptors". It is believed that carbonyls, carboxylic acids, esters, cyclic ethers, diols, polyols, furans and other oxygenates characterized by having a H:$C_{eff}$ ratio less than 2 are capable of being hydrogen acceptors, either directly or following other reactions (such as dehydration), which have converted the components to hydrogen acceptors. After accepting hydrogen, the hydrogen acceptors may be converted into species that readily dehydrate to form olefins or are capable of accepting further hydrogen. The net impact of transferring hydrogen to unsaturated oxygenates is to produce fewer paraffins and increase the aromatic hydrocarbon yield.

It is notable that carboxylic acids, in isolation, exhibit low reactivity across the condensation catalyst and evolve significant amounts of carbon dioxide for those reactions that do occur (N. Y. Chen, D. E. Walsh and L. R. Koeing, Chapter 24: Fluidized-Bed Upgrading of Wood Pyrolysis Liquids and Related Compounds, ACS Symposium Series; Amer. Chem. Soc., Washington D.C. 1988). In contrast, when reacted in the presence of other oxygenates such as alcohols, carboxylic acids readily react to form aromatics. This illustrates that only a portion of a carboxylic acid feed needs to be converted to more hydrogen rich oxygenates to facilitate the overall conversion of the carboxylic acid feedstock.

Conditioning by Hydrogenation

Figure 7:
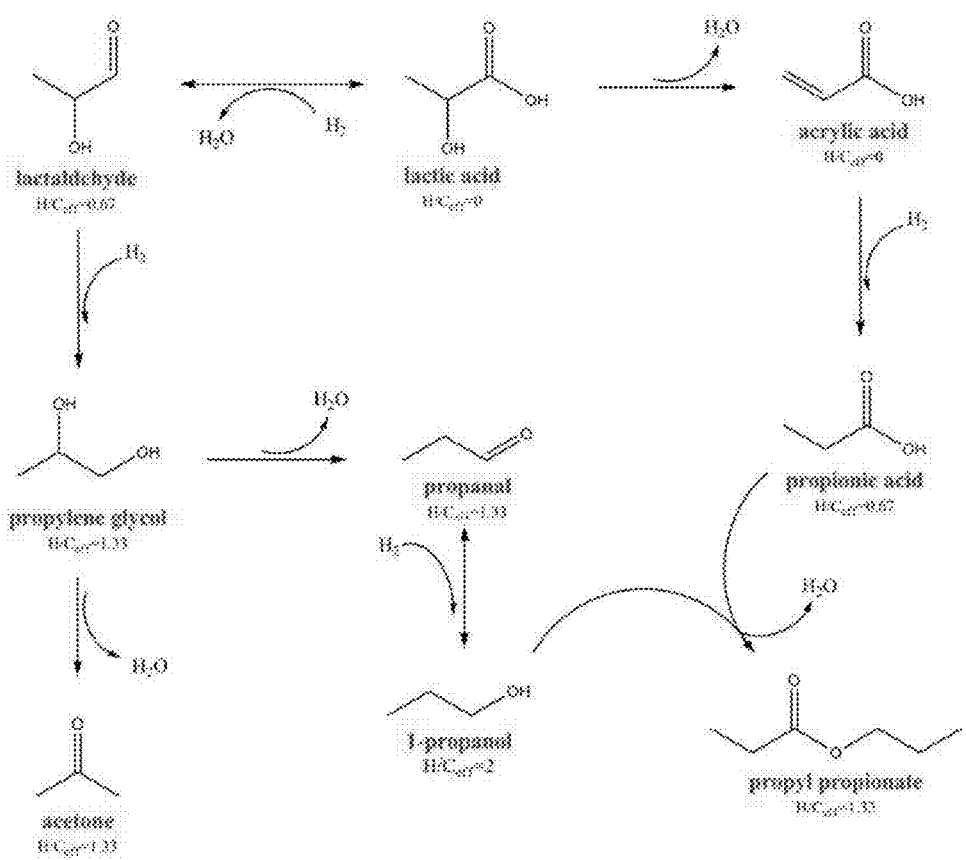
FIG. 7 is an illustration of the chemistry involved in one aspect of the present invention involving lactic acid as one component of the feedstock stream.
Figure 8:
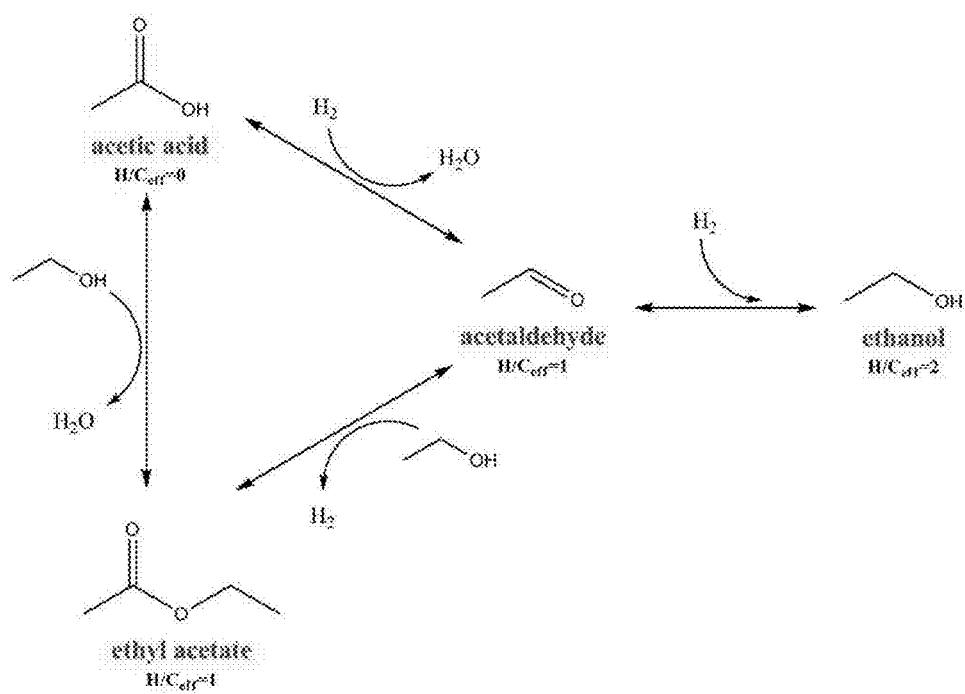
FIG. 8 is an illustration of the chemistry involved in one aspect of the present invention using acetic acid as one component of the feedstock stream.

In one embodiment, the feedstock stream includes one or more carboxylic acids, such as acetic acid or lactic acid. As illustrated in FIG. 7, the oxygenates produced from acetic acid generally include acetaldehyde, ethanol and ethyl acetate. Upon reaction, other primary carboxylic acids will produce equivalent products corresponding to the carbon number of the carboxylic acid. The specific products depend on various factors including the composition of the carboxylic acid feedstock, reaction temperature, reaction pressure, carboxylic acid concentration, the reactivity of the catalyst, and the flow rate of the carboxylic acid feedstock as it affects the space velocity (the mass/volume of reactant per unit of catalyst per unit of time).

For illustration purposes, the H:$C_{eff}$ ratio of various carboxylic acids is shown in Table 1 below.

TABLE 1

H:$C_{eff}$ Ratio of Select Carboxylic Acids

| Carboxylic Acid | H:$C_{eff}$ |
|---|---|
| Formic Acid | −2.00 |
| Acetic Acid | 0.00 |
| Propionic Acid | 0.67 |
| Butyric Acid | 1.00 |
| Isobutyric Acid | 1.00 |
| Valeric Acid | 1.20 |
| Isovaleric acid | 1.20 |
| Caproic acid | 1.33 |
| Oxalic Acid | −3.00 |
| Malonic Acid | −1.33 |
| Succinic Acid | −0.50 |
| Glutaric Acid | 0.00 |
| Adipic Acid | 0.33 |
| Glycolic Acid | −1.00 |
| Acrylic Acid | 0.00 |
| Lactic acid | 0.00 |

TABLE 1-continued

H:$C_{eff}$ Ratio of Select Carboxylic Acids

| Carboxylic Acid | H:$C_{eff}$ |
|---|---|
| Pyruvic Acid | −0.67 |
| Maleic Acid | −1.00 |
| Fumaric Acid | −1.00 |
| Glutaconic Acid | −0.40 |
| Muconic Acid | −0.33 |
| Citric Acid | −1.00 |

Paraffins generally have a H:$C_{eff}$ ratio greater than 2, while alkyl mono-aromatic compounds generally have a H:$C_{eff}$ ratio between 1 and 2, as shown in Tables 2 and 3 below.

TABLE 2

H:$C_{eff}$ Ratio of Paraffins

| Paraffins | H:$C_{eff}$ |
|---|---|
| $C_1$ | 4 |
| $C_2$ | 3 |
| $C_3$ | 2.67 |
| $C_4$ | 2.5 |
| $C_5$ | 2.4 |
| $C_6$ | 2.33 |
| $C_7$ | 2.29 |
| $C_8$ | 2.25 |
| $C_9$ | 2.22 |
| ↓ | ↓ |
| $C_\infty$ | 2 |

TABLE 3

H:$C_{eff}$ Ratio of Alkyl Substituted Mono-Aromatics

| Aromatic | H:$C_{eff}$ |
|---|---|
| Benzene | 1.0 |
| Toluene | 1.14 |
| Xylene | 1.25 |
| $C_9$ | 1.33 |
| ↓ | ↓ |
| $C_\infty$ | 2 |

When the hydrogen acceptors are passed as reactants over a condensation catalyst, an improved aromatic hydrocarbon yield is realized, relative to the yield realized when the reactants are carboxylic acids alone. The H:$C_{eff}$ ratio of the esters, aldehydes and ketones that may be formed by hydrogenation of carboxylic acids is between zero and 2 as shown in Tables 4 and 5 below.

TABLE 4

H:$C_{eff}$ Ratio of Select Esters

| Esters | H:$C_{eff}$ |
|---|---|
| Methyl Formate | 0.00 |
| Methyl Acetate | 0.67 |
| Ethyl Formate | 0.67 |
| Ethyl Acetate | 1.00 |
| Propyl Propanoate | 1.33 |
| Ethyl Lactate | 0.80 |
| Propyl Lactate | 1.00 |

TABLE 5

H:$C_{eff}$ Ratio of Aldehydes and Ketones

| Aldehydes or Ketone carbon number | H:$C_{eff}$ |
|---|---|
| $C_1$ | 0 |
| $C_2$ | 1.0 |
| $C_3$ | 1.33 |
| $C_4$ | 1.5 |
| $C_5$ | 1.6 |
| $C_6$ | 1.67 |
| $C_7$ | 1.71 |
| $C_8$ | 1.75 |
| $C_9$ | 1.78 |
| ↓ | ↓ |
| $C_\infty$ | 2 |

The H:$C_{eff}$ ratio of ethanol (and of all alcohols) is 2, as shown in Table 6 below.

TABLE 6

H:$C_{eff}$ Ratio of Alcohols

| Alcohol (by number of carbon atoms) | H:$C_{eff}$ |
|---|---|
| C | 2 |
| $C_2$ | 2 |
| $C_3$ | 2 |
| $C_4$ | 2 |
| $C_5$ | 2 |
| $C_6$ | 2 |
| $C_7$ | 2 |
| $C_8$ | 2 |
| $C_9$ | 2 |
| ↓ | ↓ |
| $C_\infty$ | 2 |

Other species include carbon dioxide ($CO_2$) with a H:$C_{eff}$ ratio of −4, carbon monoxide (CO) with a H:$C_{eff}$ ratio of −2, and carbon with a H:Ceff ratio of 0. Carbonaceous residue, or coke, that may accumulate on catalyst or other surfaces exhibits a range of H:$C_{eff}$ ratios, depending on the amount of residual hydrogen and oxygen within the coke.

In accordance with the invention, the process for converting carboxylic acids to aromatic hydrocarbons can be a two-step process (in which the hydrogenation catalyst and the condensation catalyst are separate catalysts) or a one-step process (in which the hydrogenation catalyst and the condensation catalyst are one multi-functional catalyst). When separate catalysts are provided, they may be present in separate vessels, in separate beds within a single vessel, in alternating layers in a single bed of catalyst, or physically mixed within the same bed.

The general conditioning process 104 for carboxylic acids in accordance with the present invention is as follows. A carboxylic acid feedstock is first passed into contact with hydrogen and a hydrogenation catalyst in a reactor at a hydrogenation temperature and a hydrogenation pressure, thereby producing a mixture of oxygenates. The carboxylic acid feedstock may be an essentially pure carboxylic acid stream or, alternatively, the carboxylic acid feedstock may be mixed with water and/or an alcohol to create a solution wherein the carboxylic acid concentration is greater than 1%, or greater than 5%, or greater than 10%, or greater than 20%, or greater than 30%, or greater than 40%, or greater than 50%.

Various processes are known for hydrogenating carboxylic acids. The hydrogenation catalyst generally includes Fe, Ru, Co, Pt, Pd, Ni, Re, Cu, and alloys or combinations thereof, either alone or with promoters such as Ag, Au, Cr, Zn, Mn, Mg, Ca, Cr, Sn, Bi, Mo, W, B, P, and alloys or combinations thereof. The hydrogenation catalyst may also include any one of several supports, depending on the desired functionality of the catalyst. Such supports may include carbon, silica, alumina, zirconia, titania, vanadia, ceria, silica-aluminate, zeolite, kieselguhr, hydroxyapatite, zinc oxide, magnesium oxide, chromia, and mixtures thereof.

In general, the hydrogenation reaction is carried out at hydrogenation temperatures of between about 80° C. to 350° C., and hydrogenation pressures in the range of about 50 psig to 5000 psig. The hydrogen used in the reaction may include in situ hydrogen generated from other reactions occurring in series or parallel within the reactor, external $H_2$, recycled $H_2$, or a combination thereof.

The extent to which the carboxylic acid feedstock stream is hydrogenated can be measured by the amount of molecular hydrogen consumed during hydrogenation and may range from 0.05 to 2.0 moles of molecular hydrogen consumed per mole of carboxylic acid groups in the feed. In general, the reaction should be conducted under conditions where the residence time of the carboxylic acid feedstock over the catalyst is appropriate to generate the desired oxygenates. For example, the residence time may be established at a weight hourly space velocity (WHSV) of between 0.01 and 30, or between 0.05 and 10, or between 0.1 and 5.

Desirable levels of hydrogenation depend on the composition of the carboxylic acid feedstock stream. To enhance the production of aromatics during condensation step 106, longer chain carboxylic acids must be hydrogenated to a lesser extent than short chain carboxylic acids. For an acetic acid feedstock, greater than 0.8 moles of molecular hydrogen should be consumed per mole carboxylic acid feedstock to the system during hydrogenation, and greater than 1 mole of molecular hydrogen per mole of carboxylic acid is preferred to prevent an excessive coking rate. Lower extent of hydrogenation is required as carbon chain length of the carboxylic acid increases (in the absence of other functional groups, such as hydroxyls). For a propionic acid feedstock, for example, greater than 0.2 moles of molecular hydrogen should be consumed per mole carboxylic acid feedstock during hydrogenation. Greater than 0.5 mole of molecular hydrogen per mole of carboxylic acid is preferred to prevent an excessive coking rate. For mixed carboxylic acid feedstocks, the overall extent of hydrogenation should be such that the overall $H:C_{eff}$ ratio of the resulting oxygenate stream is less than 1.8, 1.75, 1.7, 1.65, 1.6, 1.55, 1.5, 1.45, or 1.4, and greater than 0.8, 0.85, 0.9, 0.95, 1.0, 1.05, 1.1, 1.15, 1.2, 1.25, 1.3, 1.35, 1.4, 1.45, or 1.5. For example, the overall extent of hydrogenation should be such that the carbon effective ratio is between 0.8 and 1.8, or between 1.0 and 1.8, or between 1.05 and 1.75, or between 1.1 and 1.7, or between 1.15 and 1.65, or between 1.2 and 1.6. Hydrogenation extent may be controlled by varying the catalyst and operating conditions. Higher temperatures generally lead to lower equilibrium levels of hydrogenation but higher catalyst activity. Higher hydrogen partial pressure generally leads to greater levels of hydrogenation. Other components, such as additional oxygenates, like alcohols, may be added to the hydrogenation products to ensure that the overall H:Ceff ratio of the resulting oxygenate stream is achieved. In addition to the hydrogenation reactions, additional reactions may be supported during the hydrogenation step, including esterification, dehydration, and aldol condensation.

Conditioning by Dehydrogenation

Figure 9:
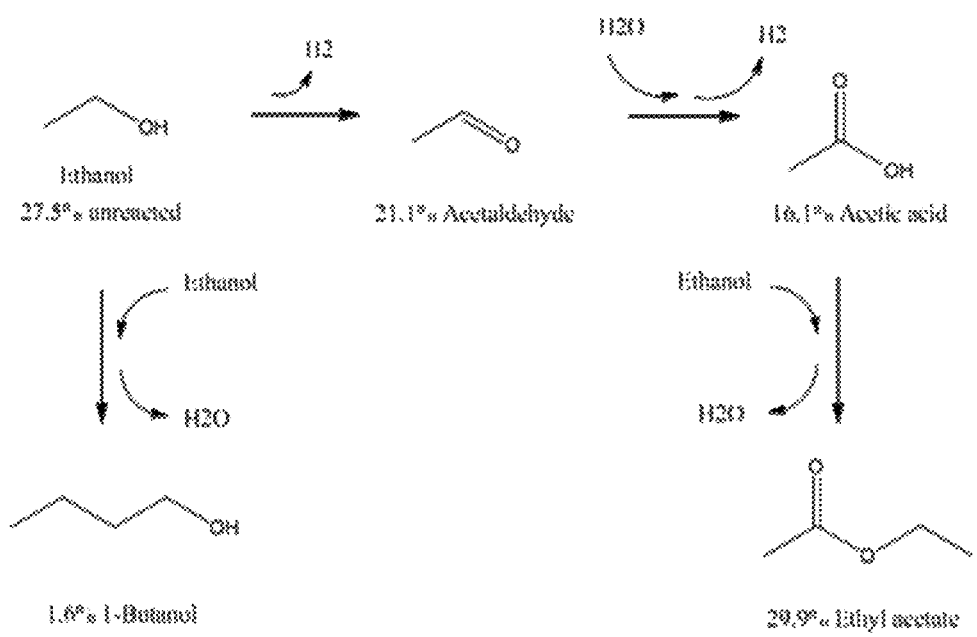
FIG. 9 is an illustration of the chemistry involved in one aspect of the present invention using ethanol as one component of the feedstock stream.
Figure 10:
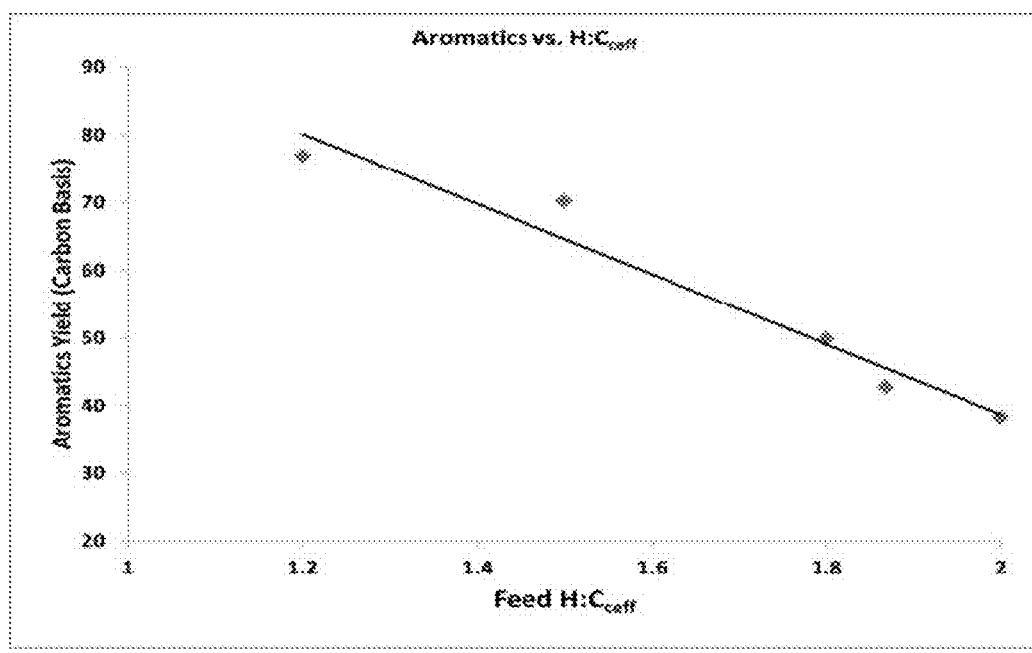
FIG. 10 is a chart illustrating expected aromatics yield based on the H:$C_{eff}$ ratio of the oxygenated mixture in accordance with the present invention.
Figure 11:
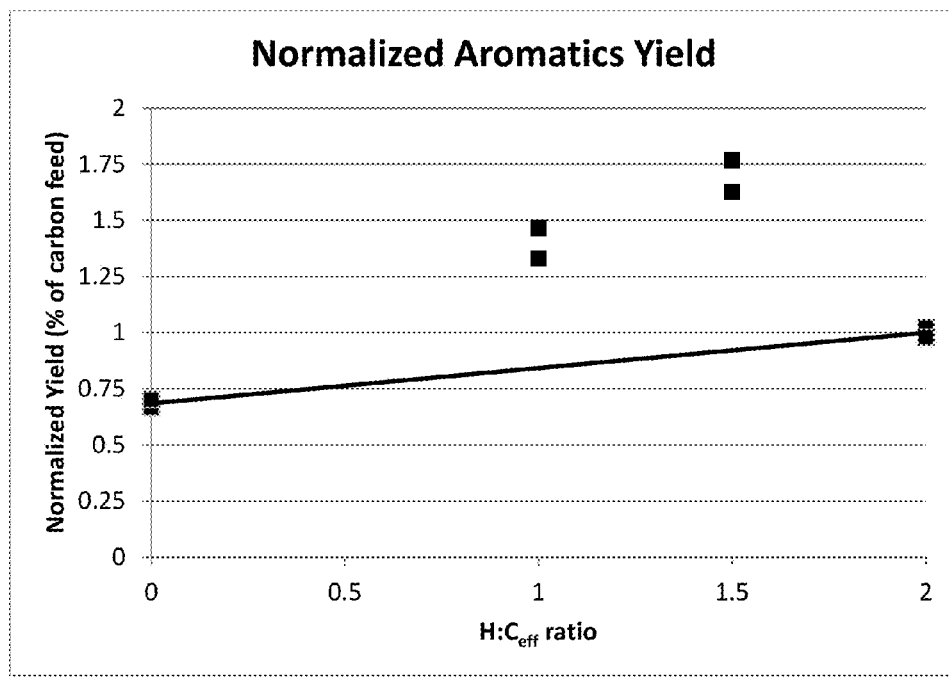
FIG. 11 is a chart illustrating the yield of aromatic hydrocarbons for mixture of acetic acid and ethanol in comparison to acetic acid only and ethanol only.

In one embodiment, the feedstock stream includes one or more alcohols, such as ethanol. As illustrated in FIG. 9, the oxygenates produced from ethanol generally include acetaldehyde, acetic acid, and ethyl acetate. Primary alcohols produce the equivalent products corresponding to the carbon number of the starting alcohol. Secondary alcohols are unable to proceed to acids or esters and will produce primarily ketones, unless used in a mixture with other alcohols. The specific products depend on various factors including the composition of the alcohol feedstock, reaction temperature, reaction pressure, alcohol concentration, the reactivity of the catalyst, and the flow rate of the alcohol feedstock as it affects the space velocity (the mass/volume of reactant per unit of catalyst per unit of time).

Ethers may also be produced from alcohols. For instance, the conversion of methanol to dimethyl ether can be used to reduce the exotherm of the condensation reaction. Dialkyl ethers may also be present in the oxygenate mixture as a product of the dehydrogenation catalyst or as a separately fed component. Dialkyl ethers, such as diethylether, dimethylether, etc., have a H:Ceff ratio of 2.0 and can impact the aromatic to paraffin ratio of the product the same as an alcohol.

As indicated previously, the H:Ceff ratio of the reactants impacts the H:Ceff ratio of the reaction products. When the hydrogen acceptors are passed as reactants over a condensation catalyst, an improved aromatic hydrocarbon yield is realized, relative to the yield realized when the reactants are alcohols alone.

In accordance with the invention, the process for converting alcohols to hydrocarbons can be a two-step process (in which the dehydrogenation catalyst and the condensation catalyst can be separate catalysts) or a one-step process (in which the dehydrogenation catalyst and the condensation catalyst can be one multi-functional catalyst). When separate catalysts are provided, they may be present in separate vessels, in separate beds within a single vessel, in alternating layers in a single bed of catalyst, or physically mixed within the same bed.

The general conditioning process step 104 for alcohol feedstock streams is as follows. An alcohol feedstock is first passed into contact with a dehydrogenation catalyst in a reactor at a dehydrogenation temperature and a dehydrogenation pressure, thereby releasing molecular hydrogen and producing the oxygenates illustrated in FIG. 9. The alcohol feedstock may be an essentially pure alcohol stream or, alternatively, the alcohol feedstock may contain water to create an aqueous solution wherein the alcohol concentration is greater than 1%, or greater than 5%, or greater than 10%, or greater than 20 wt %, or greater than 30 wt %, or greater than 40 wt %, or greater than 50 wt %, or greater than 72 wt %, or greater than 80 wt %, or greater than 90 wt %, or greater than 95 wt %. The alcohol feedstock stream may be also combined with other components to assist in arriving at the desired H:Ceff ratio.

The dehydrogenation catalyst includes one or more materials of metal and/or basic functionality capable of catalyzing the conversion of hydroxyl elements to carbonyls. Suitable metallic components include, without limitation, Cu, Ru, Ag, CuCr, CuZn, Co, Sn, Mo, and combinations thereof. Suitable base-catalyzed dehydrogenation catalysts include Li, Na, K, Cs, Mg, Ca, Ba, Zn, Ce, La, Y, Zr, hydrotalcite, base-treated aluminosilicate zeolite. The base catalyst may also include an oxide of Ti, Zr, V, Mo, Cr, Mn, Al, Ga, Co, Ni, Si, Cu, Zn, Sn, Mg, P, Fe, and combinations thereof. Preferred Group IA materials include Li, Na, K, and Cs.

Preferred Group IIA materials include Mg, Ca, and Ba. A preferred Group JIB material is Zn. Preferred Group 111B materials include Y and La. Basic resins include resins that exhibit basic functionality, such as Amberlyst A26 and Amberlyst A21. The base catalyst may be self-supporting or adhered to any one of the supports further described below, including supports containing carbon, silica, alumina, zirconia, titania, vanadia, ceria, alloys and mixtures thereof.

The base catalyst may also include zeolites and other microporous supports that contain Group IA compounds, such as Li, Na, K, and Cs. Preferably, the Group IA material is present in an amount greater than that required to neutralize the acidic nature of the support. These materials may be used in any combination, and also in combination with alumina or silica. A metal function may also be provided by the addition of group VIIIB metals, or Cu, Ga, In, Zn, Cr, or Sn.

The dehydrogenation catalyst is either self-supporting or, preferably, includes a supporting material. The support for the metallic component may contain any one or more of alumina, silica, silica-alumina, titania, carbon, zirconia, and mixtures thereof. Copper on a silica support, Raney copper, and copper-zinc-aluminate are particularly preferred dehydrogenation catalysts. For the copper catalyst on a silica support, the copper content may generally range from 0.05% to 40%, preferably from 0.1% to 20%, and most preferably from 0.2% to 10%.

In some embodiments, the dehydrogenation temperature is between about 80° C. and 500° C., preferably between about 100° C. and 450° C., and most preferably between about 150° C. and 400° C. The dehydrogenation pressure ranges from below atmospheric pressure up to about 1000 psig, preferably from about atmospheric pressure to about 700 psig, and most preferably from about 10 psig to about 500 psig.

The extent to which the alcohol feedstock stream is dehydrogenated can be measured by the amount of molecular hydrogen released during dehydrogenation and may range from 0.05 to 2.0 moles of molecular hydrogen released per mole of alcohol feed. Values greater than 1 mole of molecular hydrogen released per mole of feed are possible when carbonyls are further converted to acids, with an associated consumption of water and release of molecular hydrogen. In general, the reaction should be conducted under conditions where the residence time of the alcohol feedstock over the catalyst is appropriate to generate the desired dehydrogenation products. For example, the residence time may be established at a weight hourly space velocity (WHSV) of between 0.01 and 30, or between 0.05 and 10, or between 0.1 and 5, or between 1.0 and 4.

Desirable levels of dehydrogenation depend on the composition of the alcohol feedstock stream. To produce a shift in the aromatic-to-paraffin ratio during the oxygenate conversion, longer chain alcohols must be dehydrogenated to a greater extent than short chain alcohols. For a methanol feedstock, less than 50% dehydrogenation is desirable (0.5 moles of molecular hydrogen released per mole of total feedstock to the system), and less than 37% is preferred to prevent an excessive coking rate. For an ethanol feedstock, less than 85% dehydrogenation is desirable (0.85 moles of molecular hydrogen released per mole of total feedstock to the system), and less than 75% is preferred. For mixed alcohol feedstocks, the overall extent of dehydrogenation should be such that the overall H:Ceff ratio is less than 2.0, 1.9, 1.8, 1.7 or 1.6, and greater than 1.0, 1.1, 1.2, 1.3, 1.4 or 1.5. For example, the overall extent of dehydrogenation should be such that the carbon effective ratio is between 1.0 and 1.8, 1.1 and 1.7, or 1.2 and 1.7. For alcohols containing three or more carbons, any level up to complete dehydrogenation may be desirable. Dehydrogenation extent may be controlled by varying the catalyst and operating conditions. Higher temperatures generally lead to greater levels of dehydrogenation. Hydrogen may be added to the reaction to limit the extent of dehydrogenation and to prevent deactivation of the dehydrogenation catalyst.

Conditioning by Mixture

In another embodiment, the conditioning process step 104 includes combining a feedstock stream containing carboxylic acids with a feedstock stream containing alcohols to arrive at a oxygenate mixture having an H:Ceff ratio of between 0.8 and 1.8.

Other components, such as additional oxygenates and hydrogen, may be added to the oxygenate mixture. If additional components are added, it may be preferable to dehydrogenate smaller chain alcohols such as methanol and ethanol to a greater extent so that the overall $H:C_{eff}$ ratio is between 1.0 and 1.8, 1.1 and 1.7, or 1.2 and 1.6.

Production of Aromatics

The oxygenate mixture, including unreacted feedstock components, is then passed in whole or in part into contact with a condensation catalyst in a condensation reactor under conditions of temperature and pressure effective to convert a portion of the oxygenate mixture to aromatic hydrocarbons. In general, the condensation catalyst has one or more acidic materials capable of catalyzing the conversion of the oxygenate mixture components to the desired aromatic hydrocarbons. The condensation catalyst may include, without limitation, aluminosilicates (zeolites), silica-alumina phosphates (SAPO), aluminum phosphates (ALPO), amorphous silica alumina, zirconia, sulfated zirconia, tungstated zirconia, titania, acidic alumina, phosphated alumina, phosphated silica, sulfated carbons, phosphated carbons, heteropolyacids, and combinations thereof. In one embodiment, the catalyst may also include a modifier, such as Ce, Y, Sc, La, P, B, Bi, Li, Na, K, Cs, Mg, Ca, Ba, and combinations thereof. The catalyst may also be modified by the addition of a metal, such as Cu, Ag, Au, Pt, Ni, Fe, Co, Ru, Zn, Cd, Ga, In, Rh, Pd, Ir, Re, Mn, Mg, Cr, Mo, W, Sn, Os, alloys and combinations thereof, to provide metal functionality, and/or oxides of Ti, Zr, V, Nb, Ta, Mo, Cr, W, Mn, Re, Al, Ga, In, Fe, Co, Mg, Ni, Si, Cu, Zn, Sn, P, and combinations thereof. The condensation catalyst may be self-supporting or adhered to any one of the supports further described below, including supports containing carbon, silica, alumina, zirconia, titania, zinc oxide, magnesium oxide, aluminum phosphate, zinc aluminate, vanadia, ceria, heteropolyacids, alloys and mixtures thereof.

Ga, In, Zn, Fe, Mo, Ag, Au, Ni, P, Sc, Y, Ta, and lanthanides may also be exchanged onto zeolites to provide a zeolite catalyst. The term "zeolite" as used herein refers not only to microporous crystalline aluminosilicate but also to microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948

(highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite may be used with reactant streams containing an oxygenated hydrocarbon at a temperature of below 600° C. The zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst.

The catalyst may optionally contain any binder such as alumina, silica or clay material. The catalyst can be used in the form of pellets, extrudates and particles of different shapes and sizes. In one aspect, the condensation catalyst is ZSM-5 or beta zeolite.

In general, the condensation temperature is between about 250° C. and 550° C., preferably between about 300° C. and 500° C., and most preferably between about 320° C. and 480° C. The condensation pressure ranges from below atmospheric pressure up to about 1000 psig, preferably from about atmospheric pressure to about 700 psig, and more preferably from about 10 psig to about 500 psig. In general, the reaction should be conducted under conditions where the residence time of the oxygenate mixture over the condensation catalyst is appropriate to generate the desired aromatic hydrocarbons. For example, the residence time may be established at a weight hourly space velocity (WHSV) of between 0.01 and 30, or between 0.05 and 10, or between 0.1 and 5, or between 1.0 and 4.

Excluding molecular hydrogen ($H_2$), the overall $H:C_{eff}$ ratio of the oxygenate mixture is generally greater than 0.8 and less than 1.8, resulting in an increased yield of aromatics, and an improvement over traditional methods of converting oxygenates to aromatic hydrocarbons. When the conditioning and condensation are complete, more than 40%, or 45%, or 50%, or 60%, or 70%, or 75%, of the carbon in the carboxylic acid feedstock is contained within the aromatic hydrocarbon product.

The present invention may also be practiced as a one-step process in which the conditioning catalyst and the condensation catalyst is a multi-functional catalyst. In this approach, oxygenates are converted to hydrocarbons employing a multi-functional catalyst having one or more materials capable of catalyzing both the conditioning and condensation reactions. The multi-functional catalyst may include any of the elements suitable for separate conditioning and condensation catalysts discussed above. One particularly useful catalyst is copper loaded onto silica-bound ZSM-5. In this single-step embodiment, the conditioning reaction and the condensation reactions occur in the same reaction vessel under conditions of temperature and pressure as described above and which are suitable for both the conditioning and condensation reactions to proceed.

Aromatics Processing

In one embodiment, the present invention further includes an aromatics complex 108 for processing the aromatic hydrocarbons to provide one or more product streams containing relatively pure concentrations of benzene, toluene, xylenes (dimethylbenzenes), ethylbenzene, paraxylene, metaxylene or orthoxylene. In one embodiment, the method of the present invention is integrated with an aromatics complex, wherein the aromatics complex produces the final products distributed to the market. In some embodiments, the aromatics processing is performed in an autonomous aromatics complex, i.e., where reformate, produced elsewhere, is loaded into the aromatics complex to provide the final product streams. The term "integrated" is intended to mean that the reformate is produced at the conversion facility or within a conversion process that is linked to the aromatics complex. Preferably, to minimize production costs, the reformate is produced in close enough proximity to the aromatics complex, or includes appropriate conduits for transferring the produced reformate to the aromatics complex, thereby not requiring the reformate to be shipped. In particular embodiments, the reformate stream produced in the conversion facility is directly transferred to the aromatics complex, generally following distillation and further separation to remove product streams appropriate for other processes.

An aromatics complex is generally a combination of process units typically used to convert reformate into the basic chemical intermediates—benzene, toluene and xylenes (BTX). The xylene product, also known as mixed xylenes, contains four different $C_8$ aromatic isomers: paraxylene, orthoxylene, metaxylene and ethylbenzene. Aromatics complexes are well known in the art and can have many different configurations depending on the available reformate and the desired products. The simplest complexes produce only BTX and, for purposes of the present invention, would include one or more catalytic reforming units for producing aromatics from naptha, and one or more aromatics extraction units for the extraction of BTX.

Alternatively, the aromatics complex may be designed to maximize the yield of para-xylene and/or benzene. Such designs typically include additional units for the isomerization of xylenes sand the conversion of ethylbenzene, and units for the conversion of toluene and heavy aromatics to xylenes and benzene by toluene disproportionation and transalkylation of toluene plus $C_9$ aromatics. The principal products from this configuration are benzene, para-xylene, (optionally) metaxylene, and (optionally) ortho-xylene. If desired, a fraction of the toluene and $C_9$ aromatics can be taken as products, or some of the reformate may be used as a high-octane gasoline blending component.

Process Configurations

Figure 5:
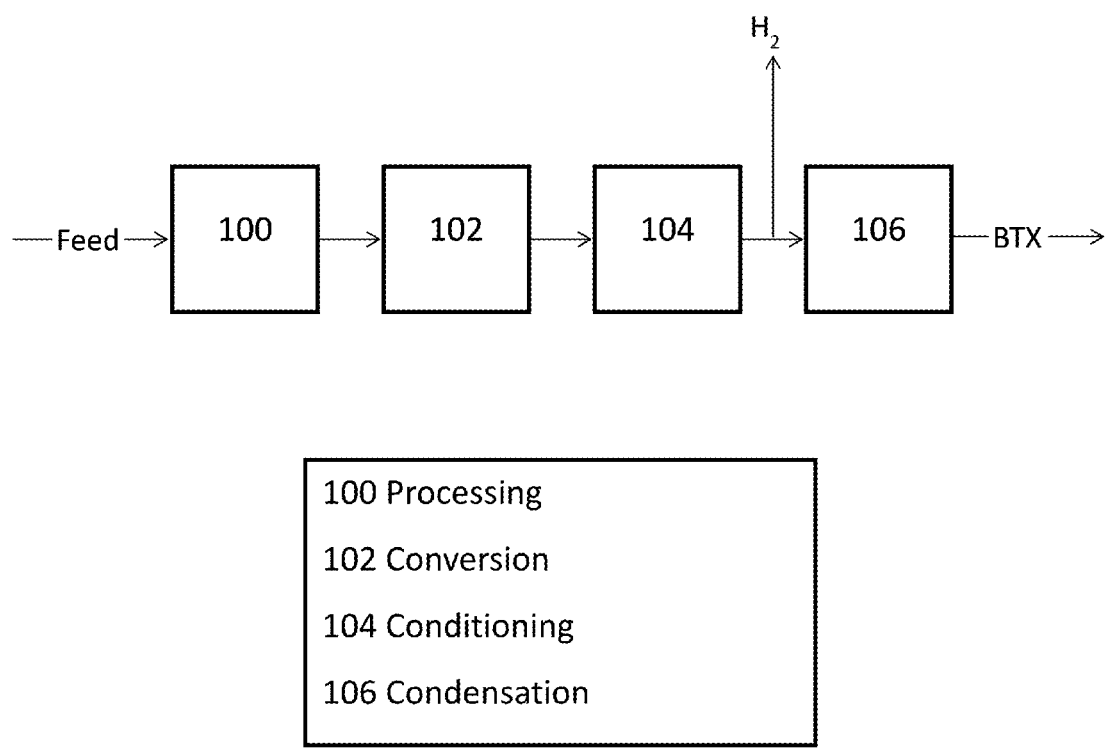
FIG. 5 is a schematic diagram of one embodiment of the present invention including a $H_2$ recovery system.

In some embodiments, the oxygenate mixture is separated to provide one or more streams which are directed to the condensation step 106 and one or more streams which are not directly fed into the condensation step. The streams which are not directly fed into the condensation step 106 may be removed from the system or recycled to the conditioning step 104 for further conversion. Means of separation include, without limitation, separation based on volatility differences between components, extraction, membranes, and ion exchange. In one preferred embodiment, the products of the conditioning step 104 are cooled and a portion of the molecular hydrogen unused in the reaction is removed as a gas phase product prior to sending the remaining components to the condensation reactor, as illustrated in FIG. 5. In another preferred embodiment, the oxygenate mixture is separated by distillation to provide an aldehyde enriched stream which is recycled to the conditioning reactor to effect conversion of the aldehydes to alcohols and esters. In yet another preferred embodiment, unreacted carboxylic acids are separated from the product stream and recycled to the conditioning reactor to increase the overall carboxylic acid conversion. In other embodiments, oxygenates other than carboxylic acids or alcohols (e.g., ketones) may be used in addition to and as a supplement to the feedstock stream.

If the carboxylic acids, ketones, aldehydes, esters, or alcohols are derived from biomass, the age of the compounds, or fractions containing the compounds, are less than 100 years old, preferably less than 40 years old, more preferably less than 20 years old, as calculated from the carbon 14 concentration of the component.

Figure 3:
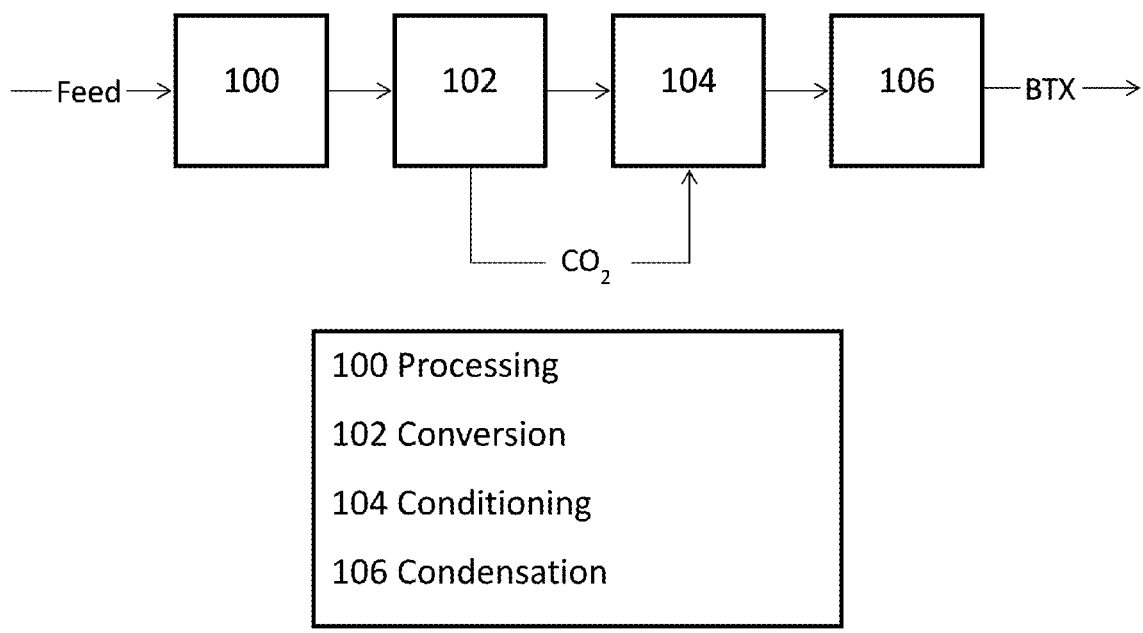
FIG. 3 is a schematic diagram of one embodiment of the present invention including a $CO_2$ recovery and methanation system for providing process heat to offset temperature reduction in the conditioning step.

Because the reaction of the conditioning step is endothermic for alcohol based intermediates, the temperature will decrease and the rate of reaction will diminish as the reaction proceeds. To make effective use of the conditioning catalyst and to minimize the size of the reactors, a minimum temperature should be maintained in the conditioning reactors. Ordinarily this might be done by reheating the reaction mixture in the conditioning reactor through heat exchange equipment supplied by a heat transfer fluid such as steam or hot oil. Referring to FIG. 3, in one embodiment, the $CO_2$ formed in 102 can be reacted with the hydrogen produced in 104 to form methane. The heat generated by the exothermic methane-forming reaction will aid in maintaining the desirable reaction temperature for the endothermic preconditioning reaction and reduce or eliminate utility load of the conditioning reactor. The heat generation rate, and therefore the temperature of the conditioning reactor 104, can be controlled by metering the $CO_2$ fed to the conditioning reaction 104. Because the conditioning reaction 104 is equilibrium limited, an additional benefit of consuming the hydrogen is that it overcomes the conversion limitations imposed by equilibrium and therefore allows conversion of more feed to products.

Figure 4:
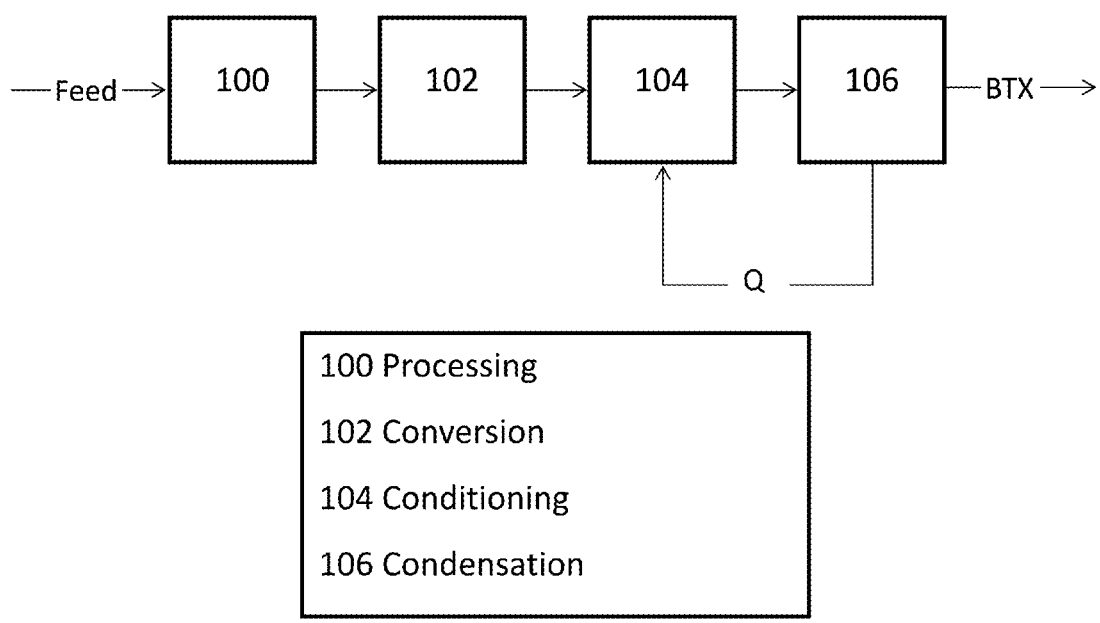
FIG. 4 is a schematic diagram of one embodiment of the present invention wherein heat from the condensation step is captured and used to provide process heat to offset temperature reduction in the conditioning step.

In another embodiment illustrated by FIG. 4, a portion of the heat required to provide the conditioning temperature is provided by heat generated in the condensation step 106. In this embodiment, the reaction mixture is reheated through direct process to process heat exchange or by a heat transfer fluid, such as steam or hot oil. The heat required may be provided directly through process to process heat exchange or indirectly to form the steam or heat the hot oil and is at least partially obtained by cooling the reaction products from the condensation step 106. Use of this source of heat will improve the process efficiency by reducing the utility duty of the plant.

Figure 6:
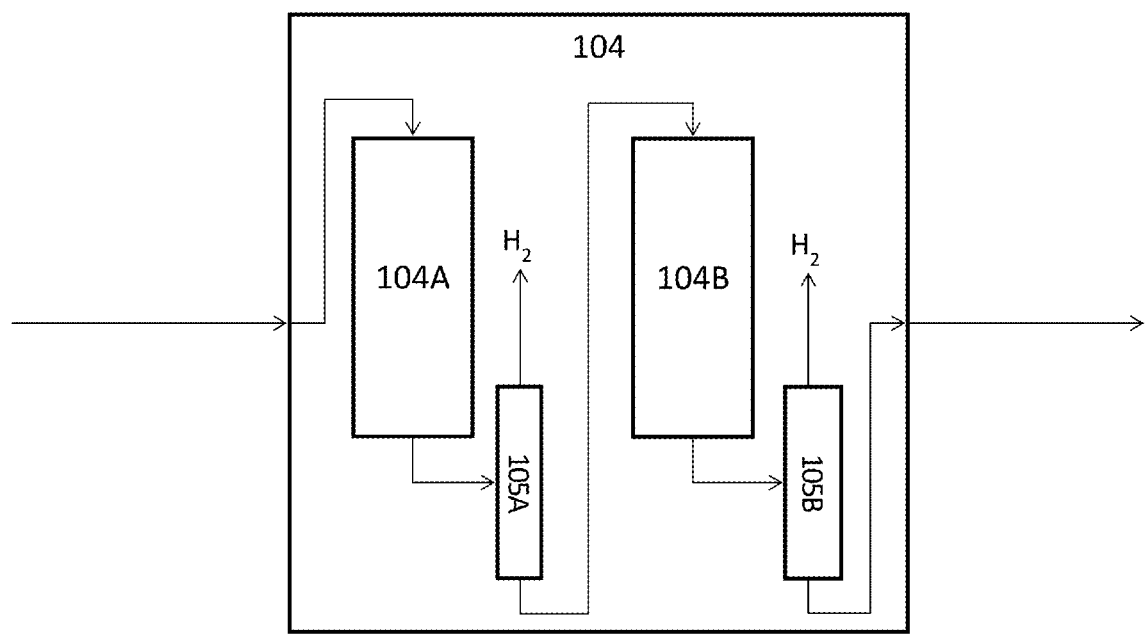
FIG. 6 is an alternative embodiment illustrating a configuration employing hydrogen capture and multiple reactors for the conditioning step of the present invention.

In most applications, the conditioning step 104 will produce hydrogen or result in unreacted hydrogen. As illustrated in FIG. 6, this hydrogen can be recovered for use elsewhere in the process, such as in catalyst reduction or for aromatics processing in an aromatics complex. The hydrogen may also be used for provide process heat as described above or simply recovered and sold as a valuable coproduct.

The conditioning step 104 may be equilibrium limited. Accordingly, the rate of reaction slows as reaction products are formed. This can limit the extent to which reactor feed is converted into products. To overcome this limitation, for conditioning steps that release hydrogen, some of the hydrogen produced by the conditioning reaction can be removed before the remaining reaction mixture after the feed to conditioning step 104 is partially converted and then fed to a subsequent stage of reaction to force formation of more desirable reaction products (see FIG. 6). This process of removing some of hydrogen after further conversion can be repeated though multiple stages. All hydrogen, including hydrogen collected from 105B, may be usefully recovered for other uses.

EXAMPLES

To demonstrate the advantage of using a mixture of oxygenates, experiments using comprising ethanol, acetic acid, and both ethanol and acetic acid were performed.

In the experiment, two Inconel reactors aligned in series were loaded with the catalyst prepared in the following manner: nickel nitrate (Sigma Aldrich, St Louis, Mo.) was added to a commercially available $Al_2O_3$-bound ZSM-5 support (1/16" extrudates, 20% $Al_2O_3$ Binder, ZSM-5 SAR 30, Zeolyst) using excess water and evaporating the water while heating at 60° C. under vacuum and rotating in a round bottom flask until dry to achieve a target Ni loading of 1 wt %. Each reactor had an internal diameter of 0.87 inches with an Inconel thermowell with an OD of 0.1875 inches running through the center of the reactor. The catalyst was loaded to a depth of 11.5 inches, accounting for 72 g of catalyst per reactor. The catalysts were heated up at atmospheric pressure flowing approximately 200 ml/min $N_2$ across the catalyst while ramping the temperatures from 25° C. to 375° C. in 2 hours. Once at temperature, the reactors were pressurized with $N_2$ to 200 psig. A compressor was turned on to provide a gas recirculation stream across these two reactors at a rate of approximately 1300 sccm. At this point, a feed mixture consisting of 80% ethanol and 20% water (by mass) was fed downflow into the first reactor at a rate of 0.63 g/min. Once steady state conditions were achieved, an analysis of reaction products was completed. The gas products were analyzed by means of a gas chromatograph equipped with a flame ionization detector, the aqueous phase products were analyzed for total carbon and with a gas chromatograph equipped with a mass spectrometry detector, and the organic phase components were analyzed using a gas chromatograph equipped with both flame ionization and mass spectrometry detectors. Four separate data points were obtained, and the results are presented in Table 7 and FIG. 4 below.

The experiment was repeated with a feed of acetic acid. In other words, the catalyst, reactors, and procedures were the same, but the $2^{nd}$ feed mixture consisted of 80% acetic acid and 20% water (by mass). Two separate data points were obtained, and the results are presented in Table 7 and FIG. 4 below.

The experiment was repeated with a feed comprising ethanol and acetic acid having a $H:C_{eff}$ ratio of 1.5. In other words, the catalyst, reactors, and procedures were the same, but the $3^{rd}$ feed mixture consisted of 56% ethanol, 24% acetic acid, and 20% water (by mass). Two separate data points were obtained, and the results are presented in Table 7 and FIG. 4 below.

The experiment was repeated again with a different feed comprising acetic acid and ethanol having a H:$C_{eff}$ ratio of 1.0. In other words, the catalyst, reactors, and procedures were the same, but the 4th feed mixture consisted of 34.7% ethanol, 45.3% acetic acid, and 20% water (by mass). Two separate data points were obtained, and the results are presented in Table 7 and FIG. 4 below.

The experiment illustrates the advantage of using a mixture of oxygenates. A straight line connects the acetic acid only and the ethanol only cases, which illustrates the expected yield from a linear combination of the individual oxygenate yields. The results illustrate the advantage of converting a mixture of oxygenates to aromatic hydrocarbons as the yield of aromatic hydrocarbons is substantially higher than would be predicted from a linear combination of the oxygenate components.

TABLE 7

Aromatic chemical yield as a function of a mixture of ethanol and acetic acid

| Feed | H:$C_{eff}$ Ratio | Aromatics Yield (% of feed Carbon) | Normalized Yield (% of feed Carbon) |
|---|---|---|---|
| Ethanol | 2.0 | 39.9% | 1.00 |
| Ethanol | 2.0 | 40.0% | 1.00 |
| Ethanol | 2.0 | 40.9% | 1.02 |
| Ethanol | 2.0 | 39.2% | 0.98 |
| Acetic Acid | 0.0 | 26.7% | 0.67 |
| Acetic Acid | 0.0 | 27.1% | 0.70 |
| Ethanol/Acetic Acid | 1.5 | 70.7% | 1.77 |
| Ethanol/Acetic Acid | 1.5 | 65.1% | 1.63 |
| Ethanol/Acetic Acid | 1.0 | 58.6% | 1.47 |
| Ethanol/Acetic Acid | 1.0 | 53.2% | 1.33 |

The invention claimed is:

1. A method for producing aromatic hydrocarbons, the method comprising:
   (a) processing a raw feedstock to form an intermediate feedstock;
   (b) converting the intermediate feedstock to a feedstock stream comprising an alcohol, a carboxylic acid, or combinations thereof;
   (c) conditioning the feedstock stream to provide an oxygenate mixture having a total H:$C_{eff}$ ratio of between 1.2 and 1.6; and
   (d) exposing the oxygenate mixture to a condensation catalyst comprising a member selected from the group consisting of aluminosilicates, silica-alumina phosphates, and aluminum phosphates to produce aromatic hydrocarbons, wherein greater than 40% of carbon in the intermediate feedstock is contained within the aromatic hydrocarbons.

2. The method of claim 1, wherein the intermediate feedstock comprises oxygenated hydrocarbons, alkanes, alkenes, $CO_x$ molecules, hydrogen, synthesis gas, or combinations thereof.

3. The method of claim 1, wherein the converting step (b) comprises fermentation, hydrogenolysis, hydrolysis, pyrolysis, aqueous phase reforming, alcohol synthesis, Fisher-Tropsch synthesis, steam reforming, partial oxygenation, or combinations thereof.

4. The method of claim 1, wherein step (b) comprises the steps of:
   fermenting the intermediate feedstock with one or more species of microorganism to form a fermentation broth comprising alcohols or carboxylic acids;
   removing the alcohols or carboxylic acids from the fermentation broth to provide the feedstock stream; and
   purifying the feedstock stream prior to exposing the oxygenate mixture to the conditioning catalyst.

5. The method of claim 1, wherein the raw feedstock is biomass, natural gas, coal, or petroleum.

6. The method of claim 1, wherein the processing step (a) comprises sugar processing, biomass deconstruction, gasification, pyrolysis, combustion, liquefaction, steam reforming, cracking, or combinations thereof.

7. The method of claim 1, wherein the alcohol is selected from the group consisting of a primary alcohol, a secondary alcohol, a polyhydric alcohol, and combinations thereof.

8. The method of claim 1, wherein the carboxylic acid is selected from the group consisting of mono-carboxylic acid, di-carboxylic acid, hydroxycarboxylic acid, and combinations thereof.

9. The method of claim 1, wherein the conditioning step (c) comprises exposing the feedstock stream to a conditioning catalyst at a conditioning temperature and a conditioning pressure to produce the oxygenate mixture or combining a portion of the feedstock stream with a portion of a second feedstock stream to produce the oxygenate mixture.

10. The method of claim 1, wherein the aromatic hydrocarbons are selected from the group consisting of benzene, toluene, orthoxylene, metaxylene, paraxylene, ethylbenzene, $C_9$ aromatics, and combinations thereof.

11. The method of claim 1, wherein the oxygenate mixture comprises two or more members selected from the group consisting of an alcohol, a carboxylic acid, an ester, a ketone, and an aldehyde.

12. The method of claim 1, wherein hydrogen is produced by step (a), step (b), step (c), step (d), or combinations thereof.

13. The method of claim 1, wherein $CO_x$ molecules are produced by step (a), step (b), step (c), step (d), or combinations thereof.

14. The method of claim 13, wherein a hydrogen stream is combined with the $CO_x$ molecules to produce hydrocarbons, alcohols, carboxylic acids, or combinations thereof.

15. The method of claim 1, wherein hydrocarbons are produced by step (a), step (b), step (c), step (d), or combinations thereof.

16. The method of claim 15, wherein an oxygen stream is combined with the hydrocarbons to produce alcohols, carboxylic acids, or combinations thereof.

17. The method of claim 1, wherein a portion of a conditioning temperature is provided by heat generated in step (d).

18. A method for producing biomass-derived aromatic hydrocarbons, the method comprising:
   (a) processing biomass to form a biomass-derived feedstock;
   (b) converting the biomass-derived feedstock to a feedstock stream comprising an alcohol or carboxylic acid;
   (c) conditioning the feedstock stream to provide an oxygenate mixture having a total H:$C_{eff}$ ratio of between 1.2 and 1.6; and
   (d) exposing the oxygenate mixture to a condensation catalyst comprising a member selected from the group consisting of aluminosilicates, silica-alumina phosphates, and aluminum phosphates at a condensation pressure and a condensation temperature to produce aromatic hydrocarbons, wherein greater than 40% of carbon in the feedstock stream is contained within the aromatic hydrocarbons.

19. The method of claim 18, wherein
step (b) comprises fermenting the biomass-derived feedstock with one or more species of microorganism to form a fermentation broth comprising alcohols or carboxylic acids and removing the alcohols or carboxylic acids from the fermentation broth to provide a feedstock stream comprising (i) one or more of a primary alcohol, methanol, ethanol, n-propanol, iso-propanol, n-butanol, 2-butanol, isobutanol, n-pentanol, n-hexanol, ethylene glycol, propylene glycol, glycerol, erythritol, threitol or sugar alcohols or (ii) one or more of a mono-carboxylic acid, a di-carboxylic acid, formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, muconic acid, itaconic acid, or citric acid;
step (c) comprises exposing the feedstock stream to a dehydrogenation catalyst at a dehydrogenation temperature and a dehydrogenation pressure to produce diatomic hydrogen and an oxygenate mixture having a total H:$C_{\mathit{eff}}$ ratio of between 1.2 and 1.6 or exposing the feedstock stream to hydrogen and a hydrogenation catalyst at a hydrogenation temperature and a hydrogenation pressure to produce an oxygenate mixture having a total H:$C_{\mathit{eff}}$ ratio of between 1.2 and 1.6; and
step (d) comprises exposing the oxygenate mixture to the condensation catalyst at a condensation pressure ranging from less than atmospheric pressure to about 1000 psig and a condensation temperature of between about 250° C. and 550° C. to produce the aromatic hydrocarbons.

20. The method of claim 18, wherein
step (b) comprises fermenting the biomass-derived feedstock with one or more species of microorganism to form a fermentation broth comprising alcohols or carboxylic acids; and removing the alcohols or carboxylic acids from the fermentation broth to provide a feedstock stream comprising (i) one or more of a primary alcohol, methanol, ethanol, n-propanol, iso-propanol, n-butanol, 2-butanol, isobutanol, n-pentanol, n-hexanol, ethylene glycol, propylene glycol, glycerol, erythritol, threitol and sugar alcohols or (ii) one or more of a mono-carboxylic acid, a di-carboxylic acid, formic acid, acetic acid, propionic acid, butyric acid, isobutyric acid, valeric acid, isovaleric acid, caproic acid, oxalic acid, malonic acid, succinic acid, glutaric acid, adipic acid, glycolic acid, acrylic acid, lactic acid, pyruvic acid, maleic acid, fumaric acid, glutaconic acid, muconic acid, itaconic acid, or citric acid;
step (c) comprises combining a portion of the feedstock stream with a portion of a second feedstock stream to provide an oxygenate mixture having a total H:$C_{\mathit{eff}}$ ratio of between 1.2 and 1.6; and
step (d) comprises exposing the oxygenate mixture to the condensation catalyst at a condensation pressure ranging from less than atmospheric pressure to about 1000 psig and a condensation temperature of between about 250° C. and 550° C. to produce the aromatic hydrocarbons.

* * * * *

UNITED STATES PATENT AND TRADEMARK OFFICE
CERTIFICATE OF CORRECTION

PATENT NO. : 9,873,836 B2  
APPLICATION NO. : 14/285158  
DATED : January 23, 2018  
INVENTOR(S) : Paul Blommel et al.

Page 1 of 1

It is certified that error appears in the above-identified patent and that said Letters Patent is hereby corrected as shown below:

In the Specification

Column 19, Line 2, "JIB" should be -- IIB --

Column 19, Line 2, "111B" should be -- IIIB --

Signed and Sealed this  
Thirtieth Day of July, 2019

Andrei Iancu  
*Director of the United States Patent and Trademark Office*